United States Patent
Marshall et al.

(10) Patent No.: US 10,458,993 B2
(45) Date of Patent: Oct. 29, 2019

(54) ASSAY FOR ASSESSING CONFORMATIONAL STABILITY OF MEMBRANE PROTEIN

(71) Applicant: Heptares Therapeutics Limited, Cambridge (GB)

(72) Inventors: Fiona Hamilton Marshall, Cambridge (GB); Seyed Ali Jazayeri-Dezfuly, Cambridge (GB); Jayesh Chhotubhai Patel, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

(21) Appl. No.: 14/404,768

(22) PCT Filed: May 31, 2013

(86) PCT No.: PCT/GB2013/051464
§ 371 (c)(1),
(2) Date: Dec. 1, 2014

(87) PCT Pub. No.: WO2013/179062
PCT Pub. Date: Dec. 5, 2013

(65) Prior Publication Data
US 2015/0147822 A1    May 28, 2015

Related U.S. Application Data

(60) Provisional application No. 61/654,265, filed on Jun. 1, 2012.

(51) Int. Cl.
| | |
|---|---|
| *G01N 33/53* | (2006.01) |
| *G01N 33/68* | (2006.01) |
| *C07K 14/72* | (2006.01) |
| *G01N 33/542* | (2006.01) |
| *G01N 33/566* | (2006.01) |
| *G01N 21/64* | (2006.01) |

(52) U.S. Cl.
CPC ....... *G01N 33/6842* (2013.01); *C07K 14/723* (2013.01); *G01N 21/6428* (2013.01); *G01N 33/542* (2013.01); *G01N 33/566* (2013.01); *G01N 2333/705* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 6,692,696 B1 | 2/2004 | Alberte | |
| 7,294,472 B2 | 11/2007 | Gilchrist et al. | |
| 7,803,559 B1 | 9/2010 | Diamond et al. | |
| 7,998,694 B2 | 8/2011 | Trinquet et al. | |
| 8,703,915 B2 | 4/2014 | Jazayeri-Dezfuly et al. | |
| 8,748,182 B2 | 6/2014 | Heal et al. | |
| 8,785,135 B2 | 7/2014 | Henderson et al. | |
| 8,790,933 B2 | 7/2014 | Weir et al. | |
| 8,900,591 B2 | 12/2014 | Hutchings et al. | |
| 9,081,020 B2 | 7/2015 | Weir et al. | |
| 9,260,505 B2 | 2/2016 | Weir et al. | |
| 10,126,313 B2 | 11/2018 | Weir et al. | |
| 10,174,101 B2 | 1/2019 | Jazayeri-Dezfuly et al. | |
| 2002/0048811 A1 | 4/2002 | Devreotes et al. | |
| 2009/0220988 A1 | 9/2009 | Trinquet et al. | |
| 2010/0190188 A1* | 7/2010 | Henderson ........... | C07K 14/723 435/7.8 |
| 2011/0027910 A1 | 2/2011 | Weir et al. | |
| 2011/0028700 A1 | 2/2011 | Heal | |
| 2011/0046351 A1 | 2/2011 | Weir et al. | |
| 2011/0112037 A1 | 5/2011 | Warne et al. | |
| 2012/0165507 A1 | 6/2012 | Jazayeri-Dezfuly et al. | |
| 2012/0270230 A1 | 10/2012 | Henderson et al. | |
| 2012/0288913 A1 | 11/2012 | Hanson et al. | |

(Continued)

FOREIGN PATENT DOCUMENTS

| | | |
|---|---|---|
| CN | 101688203 A | 3/2010 |
| EP | 1 491 207 A1 | 12/2004 |

(Continued)

OTHER PUBLICATIONS

Alexandrov et al., Microscale Fluorescent Thermal Stability Assay for Membrane Proteins; Structure; 2008;16:351-359.

Anbazhagan et al., Unfolding a transmembrane helix dimer: A FRET study in mixed micelles. Arch Biochem Biophys. Mar. 15, 2010;495(2):159-64. doi: 10.1016/j.abb.2010.01.006. Epub Jan. 13, 2010.

Bazin et al., Time resolved amplification of cryptate emission: a versatile technology to trace biomolecular interactions. J Biotechnol. Jan. 2002;82(3):233-50.

Bockaert et al., GPCR-GIP networks: a first step in the discovery of new therapeutic drugs? Curr Opin Drug Discov and Dev. 2004. 7:649-657.

Fan et al., Thermal precipitation fluorescence assay for protein stability screening. J Struct Biol. Sep. 2011;175(3):465-8. doi:10.1016/j.jsb.2011.05.003. Epub May 12, 2011.

Foord et al., International Union of Pharmacology. XLVI. G Protein-Coupled Receptor List. Pharmacol. Rev. 2005. 57:279-288.

(Continued)

Primary Examiner — Michael D Pak
(74) Attorney, Agent, or Firm — Wolf, Greenfield & Sacks, P.C.

(57) ABSTRACT

The invention provides an assay for assessing the conformational stability of a membrane protein, comprising: (a) providing a sample comprising a first population and a second population of a membrane protein; wherein the membrane protein in the first population is labelled with a donor label and the membrane protein in the second population is labelled with an acceptor label, or the membrane protein in the first population is labelled with an acceptor label and the membrane protein in the second population is labelled with a donor label, (b) exposing the first and second populations of the membrane protein to a stability modulating agent and/or condition, (c) and assessing aggregation between membrane proteins of the first and second populations by activating the donor label to permit a distance-dependent interaction with the acceptor label, which interaction produces a detectable signal.

20 Claims, 3 Drawing Sheets

(56) References Cited

U.S. PATENT DOCUMENTS

Figure 1:
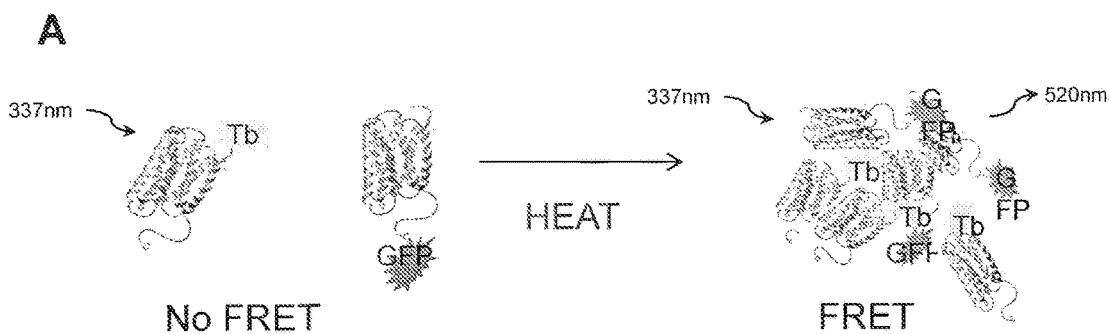
Figure 1:
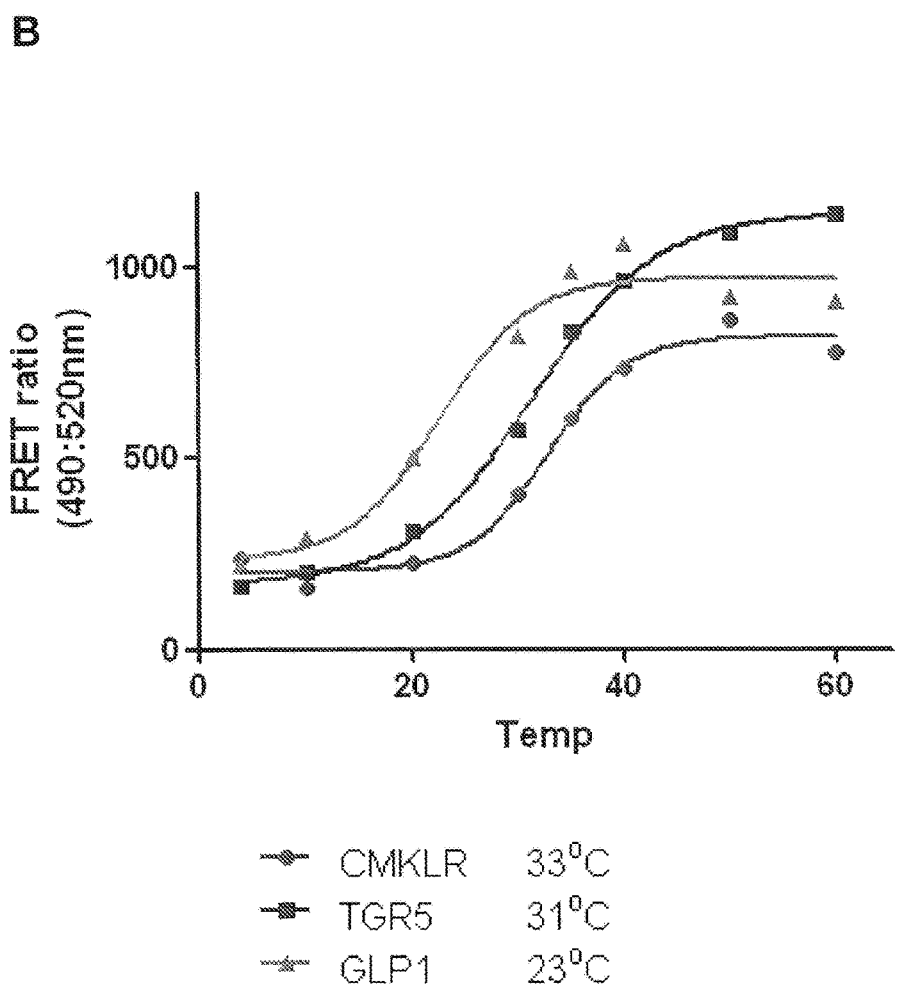

| | | | |
|---|---|---|---|
| 2013/0224238 | A1 | 8/2013 | Hutchings et al. |
| 2014/0031525 | A1 | 1/2014 | Robertson et al. |
| 2014/0315299 | A1 | 10/2014 | Jazayeri-Dezful et al. |
| 2014/0316116 | A1 | 10/2014 | Weir et al. |
| 2014/0357521 | A1* | 12/2014 | Steyaert ............ C07K 14/705 506/9 |
| 2015/0261911 | A1 | 9/2015 | Bortolato et al. |
| 2016/0052991 | A1 | 2/2016 | Henderson et al. |
| 2016/0327576 | A1 | 11/2016 | Weir et al. |
| 2017/0145075 | A1 | 5/2017 | Robertson et al. |
| 2018/0086814 | A1 | 3/2018 | Henderson et al. |
| 2019/0094247 | A1 | 3/2019 | Weir et al. |

FOREIGN PATENT DOCUMENTS

| | | |
|---|---|---|
| EP | 2450445 A1 | 5/2012 |
| JP | 2002-510790 | 4/2002 |
| JP | 2004-238384 A | 8/2004 |
| JP | 2005-503124 A | 2/2005 |
| JP | 2005-515402 | 5/2005 |
| JP | 2006-506642 | 2/2006 |
| JP | 2006-340717 A | 12/2006 |
| JP | 2007-530919 | 11/2007 |
| JP | 2009-506336 A | 2/2009 |
| JP | 2011-224018 A | 10/2011 |
| WO | WO 99/51777 | 10/1999 |
| WO | WO 2000/070343 | 11/2000 |
| WO | WO 01/58916 A2 | 8/2001 |
| WO | WO 02/083736 A2 | 10/2002 |
| WO | WO 02/092833 A2 | 11/2002 |
| WO | WO 2004/046725 A2 | 6/2004 |
| WO | WO 2005/010532 A1 | 2/2005 |
| WO | WO 2008/114020 A2 | 9/2008 |
| WO | WO 2009/051769 A1 | 4/2009 |
| WO | WO 2009/055512 A2 | 4/2009 |
| WO | WO 2009/071914 A2 | 6/2009 |
| WO | WO 2011/143575 A2 | 11/2011 |
| WO | WO 2012/030735 A1 | 3/2012 |

OTHER PUBLICATIONS

Forster, 10$^{th}$ Spiers memorial lecture. Transfer mechanisms of electronic excitation. Apr. 14, 1959. 7-17.
Kenakin, Protean agonists. Keys to active receptor states? Ann. N.Y. Acad. Sci. 1997. 812:116-125.
Keppler et al., A general method for the covalent labeling of fusion proteins with small molecules in vivo. Nat Biotechnol. Jan. 2003;21(1):86-9. Epub Dec. 9, 2002.
Keppler et al., Labeling of fusion proteins with synthetic fluorophores in live cells. Proc Natl Acad Sci U S A. Jul. 6, 2004;101(27):9955-9. Epub Jun. 28, 2004.
Knepp et al., Direct measurement of thermal stability of expressed CCR5 and stabilization by small molecule ligands. Biochemistry. Feb. 1, 2011;50(4):502-11. doi: 10.1021/bi101059w. Epub Dec. 30, 2010.
Magnani et al., Co-evolving stability and conformational homogeneity of the human adenosine A2a receptor. PNAS. 2008. 105(31):10744-10749.
Milligan et al., Protein-protein interactions at G-protein-coupled receptors. Trends Pharmacol. Sci. 2001. 22:513-518.
Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
Newman-Tancredi et al., Agonist and inverse agonist efficacy at human recombinant serotonin 5-HT1A receptors as a function of receptor:G-protein stoichiometry. Neurophamacology. 1997. 36:451-459.
Overington et al., How many drug targets are there? Natur Rev. Drug Discovery. 2006. 5:993-996.

Pollitt et al. A rapid cellular FRET assay of polyglutamine aggregation identifies a novel inhibitor. Neuron. Nov. 13, 2003;40(4):685-94.
Rajan et al., Specificity in intracellular protein aggregation and inclusion body formation. Proc Natl Acad Sci U S A. Nov. 6, 2001;98(23):13060-5. Epub Oct. 30, 2001.
Roberti et al., Fluorescence imaging of amyloid formation in living cells by a functional, tetracysteine-tagged alpha-synuclein. Nat Methods. Apr. 2007;4(4):345-51. Epub Mar. 11, 2007.
Roberts et al., Mechanisms of inverse agonist action at D2 dopamine receptors. Br. J. Pharmacol. 2005. 145:34-42.
Savinainen et al., Identification of WIN55212-3 as a competitive neutral antagonist of the human cannabinoid CB2 receptor. Br. J. Pharmacol. 2005. 145:636-645.
Selvin, The renaissance of fluorescence resonance energy transfer. Nat Struct Biol. Sep. 2000;7(9):730-4.
Serrano-Vega et al., Conformational thermostabilisation of the β-adrenergic receptor in a detergent-resistant form. PNAS. 2008 105(3):877-882.
Shibata et al. Thermostabilization of the Neurotensin Receptor NTS1, J. Mol. Biol. 2009 390(2):262-277.
Tate et al., Engineering G protein-coupled receptors to facilitate their structure determination. Curr Opin Struct Biol. Aug. 2009;19(4):386-95. doi: 10.1016/j.sbi.2009.07.004. Epub Aug. 12, 2009.
Wang et al., The renilla luciferase-modified GFP fusion protein is functional in transformed cells. Proceedings 9$^{th}$ International Symposium. Bioluminescence and Chemiluminescence. Eds. Hastings. Oct. 1996.
Xia et al., Biosensing and imaging based on bioluminescence resonance energy transfer. Curr Opin Biotechnol. Feb. 2009;20(1):37-44. doi:10.1016/j.copbio.2009.01.001. Epub Feb. 11, 2009.
Xu et al., A bioluminescence resonance energy transfer (BRET) system: application to interacting circadian clock proteins. Proc Natl Acad Sci U S A. Jan. 5, 1999;96(1):151-6.
Office Communication dated Feb. 14, 2012 for U.S. Appl. No. 12/450,358.
Office Communication dated Jul. 27, 2012 for U.S. Appl. No. 12/746,674.
Office Communication dated Aug. 1, 2012 for U.S. Appl. No. 12/921,036.
Office Communication dated Sep. 5, 2012 for U.S. Appl. No. 12/866,594.
Office Communication dated Sep. 11, 2012 for U.S. Appl. No. 12/450,358.
Office Communication dated Jan. 16, 2013 for U.S. Appl. No. 13/493,898.
Office Communication dated Jan. 28, 2013 for U.S. Appl. No. 12/809,181.
Office Communication dated Feb. 15, 2013 for U.S. Appl. No. 12/921,036.
Office Communication dated Feb. 25, 2013 for U.S. Appl. No. 12/866,594.
Office Communication dated Apr. 4, 2013 for U.S. Appl. No. 12/746,674.
Office Communication dated Apr. 12, 2013 for U.S. Appl. No. 12/450,358.
Office Communication dated Jun. 19, 2013 for U.S. Appl. No. 13/379,872.
Office Communication dated Jul. 10, 2013 for U.S. Appl. No. 12/809,181.
Office Communication dated Jul. 12, 2013 for U.S. Appl. No. 13/493,898.
Office Communication dated Jul. 22, 2013 for U.S. Appl. No. 12/866,594.
Office Communication dated Sep. 27, 2013 for U.S. Appl. No. 12/450,358.
Office Communication dated Oct. 31, 2013 for U.S. Appl. No. 13/817,858.
Office Communication dated Jan. 3, 2014 for U.S. Appl. No. 12/866,594.
Office Communication dated Jan. 27, 2014 for U.S. Appl. No. 12/450,358.

(56) References Cited

OTHER PUBLICATIONS

Office Communication dated Feb. 7, 2014 for U.S. Appl. No. 13/493,898.
Office Communication dated Mar. 11, 2014 for U.S. Appl. No. 13/817,858.
Office Communication dated Jul. 28, 2014 for U.S. Appl. No. 12/866,594.
Office Communication dated Oct. 1, 2014 for U.S. Appl. No. 13/493,898.
Office Communication dated Nov. 12, 2014 for U.S. Appl. No. 13/980,497.
Office Communication dated Feb. 11, 2015 for U.S. Appl. No. 14/255,939.
Office Communication dated Oct. 13, 2015 for U.S. Appl. No. 14/210,266.
Doré et al., Structure of class C GPCR metabotropic glutamate receptor 5 transmembrane domain. Nature. Jul. 31, 2014;511: 557-62. doi: 10.1038/nature13396. Epub Jul. 6, 2014.
Kroon-Batenburg et al., Experiences with making diffraction image data available: what metadata do we need to archive? Acta Crystallogr D Biol Crystallogr. Oct. 2014;70(Pt 10):2502-9. doi: 10.1107/S1399004713029817. Epub Sep. 30, 2014.
Wiencek, New strategies for protein crystal growth. Annu Rev Biomed Eng. 1999;1:505-34.
U.S. Appl. No. 14/989,744, filed Jan. 6, 2016, Weir et al.
U.S. Appl. No. 15/197,575, filed Jun. 29, 2016, Robertson et al.
PCT/GB2013/051464, Jan. 14, 2014, International Search Report and Written Opinion.
PCT/GB2013/051464, Dec. 2, 2014, International Preliminary Report on Patentability.
Office Communication dated Dec. 4, 2015 for U.S. Appl. No. 14/237,678.
Office Communication dated Dec. 31, 2015 for U.S. Appl. No. 13/980,497.
Office Communication dated Jan. 13, 2016 for U.S. Appl. No. 14/836,820.
Office Communication dated Mar. 9, 2016 for U.S. Appl. No. 14/210,266.
Office Communication dated Jun. 24, 2016 for U.S. Appl. No. 14/237,678.
[No Author Listed] UniProt Database Accession No. P43220. 1995.
Ault et al., Creation of GPCR-based chemical sensors by directed evolution in yeast. Protein Eng Des Sel. Jan. 2006;19(1):1-8.
Jazayeri et al., Extra-helical binding site of a glucagon receptor antagonist. Nature. Apr. 25, 2016;533(7602):274-7. doi: 10.1038/nature17414.
Kinoshita, [Application and development of structure-based drug design using X-ray analysis]. Nihon Yakurigaku Zasshi. Mar. 2007;129(3):186-90.
Heydenreich et al., Stabilization of G protein-coupled receptors by point mutations. Front Pharmacol. Apr. 20, 2015;6:82. doi: 10.3389/fphar.2015.00082. eCollection 2015.
Liu (ed), Cell Information and Regulation. China Union Medical University Press, Nov. 2003, pp. 188-189.
Wang (ed), Protein Engineering. Beijing Chemical Industry Press, May 2002, pp. 58-59.
Yu et al, Introduction to Molecular Design. Beijing Higher Education Press; Germany Springer Press; Jul. 2000, pp. 130-135.
Zhai et al, Introduction to Modern Biotechnology. Beijing Higher Education Press; Germany Springer Press; Aug. 1998, pp. 123 (paragraph 3), 127 (last paragraph), 136-140.
U.S. Appl. No. 15/716,302, filed Sep. 26, 2017, Henderson et al.
Office Communication dated Mar. 24, 2017 for Chinese Application No. 201310556727.3.
Office Communication dated Apr. 5, 2017 for U.S. Appl. No. 14/237,678.
Office Communication dated Jul. 12, 2017 for U.S Appl. No. 14/989,744.
Office Communication dated Nov. 20, 2017 for U.S. Appl. No. 15/197,575.
Office Communication dated Dec. 5, 2017 for U.S. Appl. No. 14/237,678.
U.S. Appl. No. 16/215,533, filed Dec. 10, 2018, Henderson et al.
U.S. Appl. No. 16/137,421, filed Sep. 20, 2018, Jazayeri-Dezfuly et al.
Notice of Allowance dated Jun. 20, 2018 for U.S. Appl. No. 14/237,678.
Notice of Allowance dated Jul. 5, 2018 for U.S. Appl. No. 14/989,744.
Office Communication dated Jul. 5, 2018 for U.S. Appl. No. 15/197,575.
Office Communication dated Aug. 8, 2018 for U.S. Appl. No. 15/716,302.
[No Author Listed] Allergan and Heptares Announce Global R&D and Commercialization Partnership for Novel Treatments in Alzheimer's and Other Neurological Disorders. Press Release; Apr. 7, 2016. Last accessed from <https://www.heptares.com/index.php?mact=News,cntnt01,print,0&cntnt01articleid=268&cntnt01showtemplate=false&cntnt01returnid=74> on May 5, 2016.
[No Author Listed] Guide to Pharmacology: G protein-coupled receptors. Last accessed from http://www.guidetopharmacology.org/GRAC/FamilyDisplayForward?familyId=694&familyType=GPCR on Apr. 12, 2018. 4 pages.
[No Author Listed] Heptares and Kymab enter Strategic Collaboration to Discover, Develop and Commercialise Novel Antibody Therapeutics. Press Release; Apr. 18, 2016. Last accessed from <https://www.heptares.com/index.php?mact=News,cntn101,print,0&cntnt01articleid=269&cntnt01showtemplate=false&cntnt01returnid=74> on May 5, 2016.
[No Author Listed] Heptares Awarded $5.5 Million Research & Development Grant from the US National Institute on Drug Abuse (NIDA). Press Release; Sep. 28, 2015. Last accessed from <https://www.heptares.com/index.php?mact=News,cntn101,print,0&cntnt01articleid=252&cntnt01showtemplate=false&cntnt01returnid=74> on May 5, 2016.
[No Author Listed] Heptares Enters Strategic Drug Discovery Collaboration with Pfizer Inc. focused on GPCR Targets across Multiple Therapeutics Areas. Press Release; Nov. 30, 2015. Last accessed from <https://www.heptares.com/index.php?mact=News,cntnt01,print,0&cntnt01articleid=257&cntnt01showtemplate=false&cntnt01returnid=74> on May 5, 2016.
[No Author Listed] Heptares Wins Best Established Biotech Company Award at OBN Annual Awards 2016. Press Release; Oct. 7, 2016. Last accessed from <https://www.heptares.com/index.php?mact=News,cntnt01,print,0&cntnt01articleid=278&cntnt01showtemplate=false&cntnt01returnid=74> on May 31, 2017.
[No Author Listed] Teva and Heptares Enter Agreement to Discover and Develop Novel, Small-Molecule CGRP Antagonists for Treatment of Migraine. Press Release; Nov. 25, 2015. Last accessed from <https://www.heptares.com/index.php?mact=News,cntnt01,print,0&cntnt01articleid=256&cntnt01showtemplate=false&cntnt01returnid=74> on May 5, 2016.
[No Author Listed] the Nobel Prize in Chemistry 2012. Press Release; Oct. 10, 2012. Last accessed from <https://www.nobelprize.org/nobe_prizes/chemistry/laureates/2012/press.html> on Nov. 29, 2012.
Barroso, Constitutive activation of the neurotensin receptor 1 by mutation of Phe(358) in Helix seven. Br J Pharmacol. Feb. 2002;135(4):997-1002.
Boehm et al., Chemical Probe Identification Platform for Orphan GPCRs Using Focused Compound Screening: GPR39 as a Case Example. ACS Med Chem Lett. Sep. 16, 2013;4(11):1079-84. doi: 10.1021/m1400275z. eCollection Nov. 14, 2013.
Chun et al., Fusion Partner Toolchest for the Stabilization and Crystallization of G Protein-Coupled Receptors. Structure. Jun. 2012;20(6):967-76.
Chung et al., Orphan GPCR research. Br J Pharmacol. Mar. 2008;153 Suppl 1:S339-46. Epub Dec. 10, 2007.
Garippa et al., High-throughput confocal microscopy for beta-arrestin-green fluorescent protein translocation G protein-coupled receptor assays using the Evotec Opera Methods Enzymol. 2006;414:99-120.

(56) References Cited

OTHER PUBLICATIONS

Hu et al., Identification of Surrogate Agonists and Antagonists for Orphan G-Protein-Coupled Receptor GPR139. J Biomol Screen. Aug. 2009;14(7):789-97.

Huang et al., Discovery of human antibodies against the C5aR target using phage display technology. J Mol Recognit. Jul.-Aug. 2005;18(4):327-33.

Jacob et al., Virtual screening of GPCRs: An in silico chemogenomics approach. BMC Bioinformatics Sep. 6, 2008;9:363. doi: 10.1186/1471-2105-9-363.

Kitabgi et al., Functional domains of the subtype 1 neurotensin receptor (NTS1).Peptides. Oct. 2006;27(10):2461-8. Epub Aug. 9, 2006.

Klabunde et al., Chemogenomics approaches to G-protein coupled receptor lead finding. Ernst Schering Res Found Workshop. 2006;58:31-46.

Kostenis, G Proteins in Drug Screening: From Analysis of Receptor-G Protein Specificity to Manipulation of GPCR-Mediated Signaling Pathways. Curr Pharm Des. 2006;12(14):1703-15.

Kroeze et al., PRESTO-TANGO: an open-source resource for interrogation of the druggable human GPCR-ome. Nat Struct Mol Biol. May 2015;22(5):362-369. Author manuscript.

Lee et al., Cell imaging assays for G protein-coupled receptor internalization: application to high-throughput screening. Methods Enzymol. 2006;414:79-98.

Liu et al., Structural Basis for Allosteric Regulation of GPCRs by Sodium Ions. Science. Jul. 2012;337(6091):232-6.

Mackrill, Generation, Use, and Validation of Receptor-Selective Antibodies. Methods in Molecular Biology. 2004;259:47-65.

Mathew et al., Functional fusions of T4 lysozyme in the third intracellular loop of a G protein-coupled receptor identified by a random screening approach in yeast. Protein Eng Des and Sel. Oct. 2012;26(1):59-71.

Miller et al., Engineering an ultra-thermostable β1-adrenoceptor. J Mol Biol. Oct. 28, 2011;413(3):628-638. Author manuscript (17 pages).

Milligan et al., Chimeric Gα proteins: their potential use in drug discovery. Trends Pharmacol Sci. Mar. 1999;20(3):118-124.

Mishina et al., Multiplex GPCR Assay in Reverse Transfection Cell Microarrays. J Biomol Screen. Apr. 2004;9(3):196-207.

New et al., Chimeric and Promiscuous G Proteins in Drug Discovery and the Deorphanization of GPCRs. Drug Design Reviews—Online. 2005;2:66-79.

Ngo et al., Identifying ligands at orphan GPCRs: current status using structure-based approaches. Br J Pharmacol. Oct. 2016;173(20):2934-51. doi: 10.1111/bph.13452. Epub Mar. 5, 2016.

Robas et al., Maximizing serendipity: strategies for identifying ligands for orphan G-protein-coupled receptors. Curr Opin Pharmacol. Apr. 2003;3(2):121-6.

Shiroishi, [Strategies for the structural determination of G protein-coupled receptors: from an example of histamine $H_1$ receptor]. Yakugaku Zasshi. 2013;133(5):539-47.

Vohra et al., Similarity between class A and class B G-protein-coupled receptors exemplified through calcitonin gene-related peptide receptor modelling and mutagenesis studies J R Soc Interface. Dec. 12, 2012;10(79):20120846. doi: 10.1098/rsif.2012.0846. Print Feb. 2013.

Wang et al., Establishment of a chimeric reporting system for the universal detection and high-throughput screening of a G protein-coupled receptors. Biosens Bioelectron. Mar. 15, 2009;24(7):2298-304. doi: 10.1016/j.bios.2008.11.023. Epub Dec. 7, 2008.

Wise et al., The Identification of Ligands at Orphan G-Protein Coupled Receptors. Annu Rev Pharmacol Toxicol. 2004;44:43-66.

Zhang et al., Agonist-bound structure of the human $P2Y_{12}$ receptor. Nature. May 2014;509(7498):119-22. Author Manuscript. 26 pages.

Zhang et al., Selection of Active ScFv to G-Protein-Coupled Receptor CCR5 Using Surface Antigen-Mimicking Peptides. Biochemistry. Oct. 5, 2004;43(39):12575-84.

* cited by examiner

A

No FRET        FRET

B

CMKLR    33°C
TGR5    31°C
GLP1    23°C

A

FRET → Heating → No FRET

B

|  | GLP1R/BirA | U |
|---|---|---|
| Sigmoidal dose-response (variable slope) |  | Not converged |
| Best-fit values |  |  |
| Bottom | 3474 |  |
| Top | 5305 |  |
| LogEC50 | 32.76 |  |
| HillSlope | -0.08203 |  |

ASSAY FOR ASSESSING CONFORMATIONAL STABILITY OF MEMBRANE PROTEIN

RELATED APPLICATIONS

This application is a national stage filing under 35 U.S.C. § 371 of international application PCT/GB2013/051464, filed May 31, 2013, entitled "Assays," which claims the benefit under 35 U.S.C. § 119(e) of U.S. Provisional Application Ser. No. 61/654,265, entitled "Assays," filed on Jun. 1, 2012, each of which is herein incorporated by reference in its entirety.

The present invention relates to assays for assessing the stability of a membrane protein, especially a G protein-coupled receptor (GPCR).

Over the past 20 years the rate of determination of membrane protein structures has gradually increased, but most success has been in crystallising membrane proteins from bacteria rather than from eukaryotes. Bacterial membrane proteins have been easier to overexpress using standard techniques in *Escherichia coli* than eukaryotic membrane proteins [1] and the bacterial proteins are sometimes far more stable in detergent, detergent-stability being an essential prerequisite to purification and crystallisation. Apart from the difficulties in overexpressing eukaryotic membrane proteins, they often have poor stability in detergent solutions, which severely restricts the range of crystallisation conditions that can be explored without their immediate denaturation or precipitation. Ideally, membrane proteins should be stable for many days in any given detergent solution, but the detergents that are best suited to growing diffraction-quality crystals tend to be the most de-stabilising detergents i.e. those with short aliphatic chains and small or charged head groups. It is also the structures of human membrane proteins that we would like to solve, because these are required to help the development of therapeutic agents by the pharmaceutical industry. There is thus an overwhelming need to develop a generic strategy that will allow the production of detergent-stable eukaryotic integral membrane proteins for crystallisation and structure determination and potentially for other purposes such as drug screening, bioassay and biosensor applications.

GPCRs constitute a very large family of proteins that control many physiological processes and are the targets of many effective drugs. Accordingly, they are of considerable pharmacological importance. A list of GPCRs is given in Foord et al (2005) *Pharmacol Rev.* 57, 279-288, which is incorporated herein by reference. GPCRs are generally unstable when isolated, and despite considerable efforts, few crystal structures exist.

GPCRs are druggable targets, and reference is made particularly to Overington et al (2006) *Nature Rev. Drug Discovery* 5, 993-996 which indicates that over a quarter of present drugs have a GPCR as a target.

GPCRs are thought to exist in multiple distinct conformations which are associated with different pharmacological classes of ligand such as agonists and antagonists, and to cycle between these conformations in order to function (Kenakin T. (1997) *Ann N Y Acad Sci* 812, 116-125).

We have realised that there are two serious problems associated with trying to crystallise GPCRs, namely their lack of stability (eg in detergent) and the fact that they exist in multiple conformations. In order to function, GPCRs have evolved to cycle through at least two distinct conformations, the agonist-bound form and the antagonist-bound form, and changes between these two conformations can occur spontaneously in the absence of ligand. It is thus likely that any purified receptors populate a mixture of conformations. Just adding ligands to GPCRs during crystallisation trials has not resulted in their structure determination.

We found that stabilised receptors (StaRs) can be generated through a systematic mutagenesis scan throughout the whole receptor combined with a thermostability assay based on ligand binding. The method of StaR generation results in the stabilisation of a specific conformation of receptor. A detailed description of the method can be found elsewhere [2, 3, 4] and in WO 2008/114020 and WO 2009/071914. Briefly, in order to stabilise the receptors in a particular conformation, the solubilised receptor is incubated with an excess amount of either the agonist or antagonist, depending on the desired conformation. The receptor/ligand complex is then heated at various temperatures for a certain length of time. Following the heating, the excess unbound ligand is separated from receptor/ligand complexes. The percentage of ligand binding at any given temperature is used as readout for the amount of folded receptor remaining following heating. Plotting this data against temperature produces a thermal decay curve and the Tm value is defined as the temperature at which 50% of receptor activity is retained. This process relies on the availability of a good ligand with high affinity and favourable properties in detergent. However, in some cases such a ligand is not available and so an assay that circumvents the need for a ligand, i.e. where ligand binding activity is not used to measure receptor activity, is highly desirable.

Historically, structural changes of proteins during heating have been studied by various analytical techniques, such as sedimentation velocity, differential scanning calorimetry, dynamic light scattering, circular dichroism spectroscopy, UV/VIS spectroscopy, electrophoresis, fluorescence and NMR. However, these techniques often require large amounts of protein, are difficult to adapt to high-throughput screening, and often suffer from poor signal-to-noise ratios due to high background noise from detergents.

Another method for measuring the thermal stability of membrane proteins without the use of a ligand has been described by Alexandrov et al [5]. This relies on the accessibility of native cysteine residues to covalent modification as a readout for the unfolding process. Protein unfolding results in the exposure of embedded cysteines which makes them prone to modification with a reactive fluorescent probe. In the known assay the authors use the sulfhydryl-specific fluorochrome N-[4-(7-diethylamino-4-methyl-3-coumarinyl)phenyl]maleimide (CPM) because it exhibits little fluorescence in its unbound form. A major disadvantage of this assay, however, is that it is unsuitable for high throughput applications. It requires quite large quantities of a highly pure membrane protein preparation because the detection system is not specific for the membrane protein.

Knepp et al (Biochemistry 50(4): 502-11, 2011) describe the use of Fluorescence Resonance Energy Transfer (FRET) [6] to assess membrane protein stability. FRET relies on the distance-dependent transfer of energy from a donor fluorophore to an acceptor fluorophore. Importantly, donor and acceptor fluorophores must have well separated emission spectra, but the emission spectrum of the donor must overlap with the excitation spectrum of the acceptor fluorophore. In Knepp et al's method, binding of a monoclonal antibody labelled with a FRET acceptor is used as a marker of GPCR denaturation. A FRET signal is generated when the FRET acceptor is in the proximity of the FRET donor attached to the C-terminus of the GPCR. A significant limitation of this method, however, is that it requires the availability of suitable antibodies specific for the membrane protein in question. Also, the method of Knepp et al is unlikely to identify stabilising mutations that happen to be in the antibody binding site since these mutations will reduce or abolish the antibody binding. Additionally, mutations in the antibody binding site may increase the affinity of the antibody for the receptor without necessarily increasing conformational stability, thereby leading to false positives. Another disadvantage of Knepp et al's method is that the antibody may have a specific effect on the pharmacology of the GPCR. For example, the antibody may be a particular conformation of the GPCR that is not desired.

Hence, there remains a great need for a simple effective assay which can be used to measure the stability of membrane proteins.

Protein aggregation upon unfolding is a general feature of all proteins that occurs to varying degrees in different proteins. It is accepted that the overall structural stability of a protein is inversely proportional to the levels of aggregation. Membrane proteins are known to exhibit high levels of aggregation after solubilisation and more so after denaturation.

There are various methods available for measuring aggregation, but not for measuring membrane protein aggregation following denaturation.

For example, Pollitt et al (Neuron 40: 685-694, 2003) and U.S. Pat. No. 7,803,559 describe a cell-based assay to measure intracellular polyglutamine protein aggregation using FRET, and discuss its use in screening for aggregation regulators that may have therapeutic application in neurodegenerative diseases. Also, Roberti et al (Nature Methods 4(4): 345, 2007) and Rajan et al (PNAS 98(23): 13060-13065) describe FRET based methods for assessing the aggregation of proteins that are known to form aggregates as part of a disease pathology.

Protein aggregation may also be measured by the analytical techniques mentioned above. However, all of these methods demand highly purified protein Despite the above advances, methods for measuring the aggregation of membrane proteins are not widely available. This is mainly because these methods require large amounts of highly purified protein and generating highly purified membrane protein is challenging.

The present inventors have now identified methods for directly assessing aggregation of membrane proteins. Such methods allow one to identify the conditions and mutations that can minimise overall aggregation of the proteins. Compared to methods that indirectly measure aggregation such as that of Knepp et al, the present methods are believed to identify more mutations and conditions that can minimise aggregation of proteins. This is because some mutations and conditions may reduce protein aggregation without changing the structure of the protein in a way that would lead to a change in ligand binding or antibody binding, as is relied on as a read out for aggregation in the indirect methods.

According to a first aspect of the invention there is provided an assay for assessing the conformational stability of a membrane protein, comprising:

(a) providing a sample comprising a first population and a second population of a membrane protein; wherein the membrane protein in the first population is labelled with a donor label and the membrane protein in the second population is labelled with an acceptor label, or the membrane protein in the first population is labelled with an acceptor label and the membrane protein in the second population is labelled with a donor label, (b) exposing the first and second populations of the membrane protein to a stability modulating agent and/or condition, (c) and assessing aggregation between membrane proteins of the first and second populations by activating the donor label to permit a distance-dependent interaction with the acceptor label, which interaction produces a detectable signal.

In this assay, aggregation of the membrane proteins from the first and second populations is detected by virtue of the donor labels and acceptor labels coming into proximity with each other, and thereby generating a detectable signal, when the membrane proteins aggregate. If the membrane proteins are stable, there is less aggregation upon exposure to a destabilising agent and/or condition and so less signal, whereas if the membrane proteins are unstable, there is more aggregation upon exposure to a destabilising agent and/or condition and so more signal.

By "conformational stability" we include the meaning of the stability of a particular conformation of a membrane protein (eg GPCR). The stability of a particular conformation refers to how well that particular conformation can retain its structure when exposed to a denaturant or denaturing conditions. Thus, a membrane protein with high conformational stability will have an extended lifetime of a particular conformation compared to the lifetime of a particular conformation of a membrane protein with low conformational stability. Examples of denaturants/denaturing conditions include heat, detergent, a chaotropic agent and an extreme of pH, as described further below. As is well known in the art, such denaturants or denaturing conditions can affect secondary and tertiary structures of a protein but not the primary sequence.

By "membrane protein" we mean a protein that is attached to or associated with a membrane of a cell or organelle. Preferably, the membrane protein is an integral membrane protein that is permanently integrated into the membrane and can only be removed using detergents, non-polar solvents or denaturing agents that physically disrupt the lipid bilayer.

Most preferably, the membrane protein is a GPCR.

Suitable GPCRs for use in the practice of the invention include, but are not limited to chemokine receptor, (eg CCR5), β-adrenergic receptor, adenosine receptor (eg $A_{2a}$ receptor), and neurotensin receptor (NTR). Other suitable GPCRs are well known in the art and include those listed in Hopkins & Groom supra. In addition, the International Union of Pharmacology produce a list of GPCRs (Foord et al (2005) *Pharmacol. Rev.* 57, 279-288, incorporated herein by reference and this list is periodically updated at http://www.iuphar-db.org/GPCR/ReceptorFamiliesForward). It will be noted that GPCRs are divided into different classes, principally based on their amino acid sequence similarities. They are also divided into families by reference to the natural ligands to which they bind. All GPCRs are included in the scope of the invention.

Thus, the GPCR may be any of an adenosine receptor, a β-adrenergic receptor, a neurotensin receptor, a muscarinic acid receptor, a 5-hydroxytryptamine receptor, an adrenoceptor, an anaphylatoxin receptor, an angiotensin receptor, an apelin receptor, a bombesin receptor, a bradykinin receptor, a cannabinoid receptor, a chemokine receptor, a cholecystokinin receptor, a dopamine receptor, an endothelin receptor a free fatty acid receptor, a bile acid receptor, a galanin receptor, a motilin receptor, a ghrelin receptor, a glycoprotein hormone receptor, a GnRH receptor, a histamine receptor, a KiSS1-derived peptide receptor, a leukotriene and lipoxin receptor, a lysophospholipid receptor, a melanin-concentrating hormone receptor, a melanocortin receptor, a melatonin receptor, a neuromedin U receptor, a neuropeptide receptor, a N-formylpeptide family receptor, a nicotinic acid receptor, an opiod receptor, an opsin-like receptor, an orexin receptor, a P2Y receptor, a peptide P518 receptor, a platelet-activating factor receptor, a prokineticin receptor, a prolactin-releasing peptide receptor, a prostanoid receptor, a protease-activated receptor, a relaxin receptor, a somatostatin receptor, a SPC/LPC receptor, a tachykinin receptor, a trace amino receptor, a thryotropin-releasing hormone receptor, an urotensin receptor, a vasopressin/oxytocin receptor, an orphan GPCR, a calcitonin receptor, a corticotropin releasing factor receptor, a glucagon receptor, a parathyroid receptor, a VIP/PACAP receptor, a LNB7TM receptor, a GABA receptor, a metabotropic glutamate receptor, and a calcium sensor receptor (see Table 1 of Foord et al (2005) *Pharmacol. Rev.* 57, 279-288, incorporated herein by reference).

The GPCR may also be selected from any of the GPCRs listed in Table A hereinafter.

Also, other membrane proteins for which the methods of the invention may usefully be employed to measure stability include the orphan receptors listed in Table B hereinafter.

The amino acid sequences (and the nucleotide sequences of the cDNAs which encode them) of many membrane proteins (eg GPCRs are readily available, for example by reference to GenBank. In particular, Foord et al supra gives the human gene symbols and human, mouse and rat gene IDs from Entrez Gene (accessible online at ncbi.nlm.nih.gov/entrez). It should be noted, also, that because the sequence of the human genome is substantially complete, the amino acid sequences of human membrane proteins (eg GPCRs) can be deduced therefrom.

Although the membrane protein (eg GPCR) may be derived from any source, it is particularly preferred if it is from a eukaryotic source. It is particularly preferred if it is derived from a vertebrate source such as a mammal or a bird. It is particularly preferred if the membrane protein (eg GPCR) is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell (eg prokaryotic or eukaryotic host cell) subsequently. Thus, it will be plain that a eukaryotic membrane protein (eg GPCR) (such as an avian or mammalian membrane protein) may be expressed in a prokaryotic host cell, such as *E. coli*, but be considered to be avian- or mammalian-derived, as the case may be.

In some instances, the membrane protein may be composed of more than one different subunit. For example, the calcitonin gene-related peptide receptor requires the binding of a single transmembrane helix protein (RAMP1) to acquire its physiological ligand binding characteristics. Also, effector, accessory, auxiliary or GPCR-interacting proteins which combine with the GPCR to form or modulate a functional complex are well known in the art and include, for example, receptor kinases, G-proteins and arrestins (Bockaert et al (2004) *Curr Opinion Drug Discov and Dev* 7, 649-657).

The membrane proteins (eg GPCRs) may be prepared by any suitable method. Conveniently, the membrane protein is encoded by a suitable nucleic acid molecule and expressed in a suitable host cell. Suitable nucleic acid molecules encoding the membrane protein (eg GPCR) may be made using standard cloning techniques, site-directed mutagenesis and PCR as is well known in the art. Suitable expression systems include constitutive or inducible expression systems in bacteria or yeasts, virus expression systems such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris, Spodoptera frugiperda* and *Trichoplusiani* cells. Suitable animal host cells include HEK 293, COS, S2, CHO, NSO, DT40 and so on. It is known that some membrane proteins (eg GPCRs) require specific lipids (eg cholesterol) to function. In that case, it is desirable to select a host cell which contains the lipid. Additionally or alternatively the lipid may be added during isolation and purification of the membrane protein. It may also be desirable to add a ligand of the membrane protein (eg GPCR) as explained further below.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

The sample comprising the first population and second population of a membrane protein may be any suitable sample that contains the two populations. By "population" we include a plurality of the same specific type of membrane protein, as opposed to a mixture of different proteins. For example, the population may comprise at least 2, 5, 10, 50, 100, 200, 500, 1000, 5000, 10000, 100000, $10^6$, $10^7$, $10^8$, $10^9$, $10^{10}$, $10^{11}$, $10^{12}$, $10^{13}$ or $10^{14}$ protein molecules, or more. It will be appreciated that the precise number of protein molecules may depend on the expression level of the particular membrane protein and this may differ from protein to protein.

It is preferred if the populations of membrane protein (eg GPCR) are provided in a suitable solubilised form in which the membrane proteins maintain structural integrity and are in a functional form (eg are able to bind ligand). An appropriate solubilising system, such as a suitable detergent (or other amphipathic agent) and buffer system is used, which may be chosen by the person skilled in the art to be effective for the particular protein. Typical detergents which may be used include, for example, dodecylmaltoside (DDM) or CHAPS or octylglucoside (OG) or many others. In an embodiment, the sample comprises one or more detergents selected from DDM; $C_{11}$-, $C_{10}$-, $C_9$- or $C_8$-maltoside or glucoside; LDAO; and SDS. It may be convenient to include other compounds such as cholesterol hemisuccinate or cholesterol itself or heptane-1,2,3-triol. The presence of glycerol or proline or betaine may be useful. It is important that the membrane protein (eg GPCR), once solubilised from the membrane in which it resides, must be sufficiently stable to be assayed. For some membrane proteins (eg GPCRs), DDM will be sufficient, but glycerol or other polyols may be added to increase stability for assay purposes, if desired. Further stability for assay purposes may be achieved, for example, by solubilising in a mixture of DDM, CHAPS and cholesterol hemisuccinate, optionally in the presence of glycerol. For particularly unstable membrane proteins (eg GPCRs), it may be desirable to solubilise them using digitonin or amphipols or other polymers which can solubilise membrane proteins directly from the membrane, in the absence of traditional detergents and maintain stability typically by allowing a significant number of lipids to remain associated with the membrane protein. Nanodiscs may also be used for solubilising extremely unstable membrane proteins in a functional form.

Typically, the membrane protein is provided in a crude extract (eg of the membrane fraction from the host cell in which it has been expressed, such as *E. coli* or HEK293T cells). It may be provided in a form in which the membrane protein comprises at least 75%, or at least 80% or 85% or 90% or 95% or 98% or 99% of the protein present in the sample. Alternatively, the membrane protein may be provided in a semi-purified form as described in Example 1 wherein the membrane protein of interest is not the most abundant species in the sample. Thus, the membrane protein may be provided in a sample where only 5-50% of the total protein in the sample is the membrane protein (eg at least 5% or 10% or 15% or 20% or 25% or 30% or 35% or 40% or 45% of the protein present in the sample). However, for the assay of the first aspect of the invention, some purification of the membrane protein following its expression is generally required and so the crude lysate cannot normally be used. Any suitable protein purification method may be used as is standard practice in the art. Of course, it is typically solubilised as discussed above, and so the membrane protein is usually associated with detergent molecules and/or lipid molecules.

Conveniently, the first and second populations of the membrane protein are expressed and labelled separately. The populations may also be solubilised and/or purified separately as discussed above. The first and second populations of the membrane protein are then mixed together to obtain a sample. Preferably, the first population and second population of the membrane protein are present in the sample in a 1:1 molar ratio. However, it is appreciated that for small scale protein purifications, it may be difficult to measure the concentrations of proteins and so a 1:1 molar ratio is typically approximated by a 1:1 volume ratio. The approximation is believed to be close since size differences between the two populations are expected to be small and the purification efficiency is thought to be the same. Conveniently, a 1:1 volume ratio is achieved by solubilising an equal number of cells from a first population of cells expressing the membrane protein and a second population of cells expressing the membrane protein, purifying the membrane proteins from each population identically and eluting the purified protein in the same volume. The eluates are then mixed in equal volumes, so for example 250 µl of the first population is mixed with 250 µl of the second population and so on.

It will be appreciated that one of the populations of membrane proteins in the sample will be labelled with a donor label (not an acceptor label) and the other of the populations of membrane proteins will be labelled with an acceptor label (not a donor label). By 'donor label' and 'acceptor label' we include the meaning of any pairs of labels, where activation of the donor label permits a distance-dependent interaction with the acceptor label, which interaction produces a detectable signal. In this way, the detectable signal generated by interaction of donor and acceptor pairs can be used as a readout of the level of aggregation between membrane proteins from the first and second populations, and therefore conformational stability.

Conveniently, the interaction between the donor label and acceptor label involves the transfer of energy from the donor label to the acceptor label. For example, the term resonance energy transfer relates to a method where a donor label is in a close vicinity to an acceptor label. This generates an energy flow from the donor to the acceptor leading to a detection scheme where a signal is monitored through the donor or acceptor. Such a method is well known for example in a luminescence resonance energy transfer system where the donor dye can be a down or up converting label. The donor is excited and as a consequence of the proximity principle the acceptor label is excited by the donor compound and a signal is detected at the emission wavelength of the acceptor compound. There are a number of resonance energy transfer methods such as fluorescence, phosphorescence, time-resolved fluorescence, bioluminescence and luminescence resonance energy transfer. The resonance energy transfer can be realised as a signal generating method or a method where the signal is quenched. In the case of quenching, any element can be used to quench signal such as a dye or metal. In such a case, typically the emission wavelength of the donor molecule is detected. Typical metal chelating or complexing agents or ligands used in time-resolved fluorometry are 3-(2-thienoyl)-1,1,1-trifluoroacetone, 3-benzoyl-1,1,1-trifluoroacetone, coproporphyrins, porphyrins, 3-naphthoyl-1,1,1-trifluoroacetone, 2,2-dimethyl-4-perfluorobutyoyl-3-butanone, 2,2'-dipyridyl, phenanthroline, salicylic acid, phenanthroline carboxylic acid, aminophenanthroline, diphenylphenantroline, dimethylphenanthroline, bipyridylcarboxylic acid, aza crown ethers, trioctylphosphine oxide, aza cryptands, dibenzoylmethane, dinaphtoylmethane, dibiphenoylmethane, benzoylacetonato, phenylazodibenzoylmethane, dithienylpropanedione, 4,4'-bis(N,N-dimethylamino)benzophenone, tris(6,6,7,7,8,8,8-heptafluoro-2,2-dimethyloctane-3,5-dione, (alkyloxyphenyl)pyridine-2,6-dicarboxylic acid and their derivatives. Metal ions can be, for example, lanthanide or ruthenium ions. (Selvin P. Nature Struc. Biol. 2000:7; 730; Forster T. Discuss. Faraday Soc. 1959:27; 7; Latva M. Academic Dissertation, University of Turku, Finland, 1997; Mukkala V.-M. Academic Dissertation, University of Turku, Finland, 1993; Wohrle D. and Pomogailo A. D. Metal Complexes and Metals in Macromolecules, John Wiley & Sons, 2003).

In a preferred embodiment, the interaction between the donor and acceptor labels involves fluorescence energy transfer (FRET), a phenomenon whereby when donor and acceptor fluorophores are in close proximity, the fluorescence energy of the donor fluorophore transfers to the acceptor fluorophore, and luminescence of the acceptor fluorophore is observed. Any suitable pair of donor and acceptor fluorophores may be used as the donor and acceptor labels.

A particularly preferred donor fluorophore is a lanthanide, such as europium, terbium, samarium or dysprosium. Lanthanides have long lifetimes that enable time-resolved measurement of acceptor emission. This is important because it significantly decreases the effect of autofluorescence from biological material and possible direct acceptor excitation. Also, the emission peaks of lanthanides are well separated, narrow and exhibit long Stokes' shifts (the distance between the maximum absorption and emission wavelengths).

The acceptor fluorophore may be any fluorophore with an excitation wave length that overlaps with one of the emission peaks of the donor. For the emission peaks of the lanthanide chelates see Table 1, the dominant peak is shown in bold. For example, with Terbium donor, any fluorophore with the excitation wave length around 490 nm, 545 nm or 620 nm could be used. Hence, a fluorophore such as Fluorescein, Rhodamine, Alexa Fluora 488, Dylight 488, d2, Cy3, BODIPY FL, BODIPY 630/650-X, red-shifted variants of green fluorescent protein (GFP), typified by EGFP and GFP-S65T, may be used in combination with Terbium.

TABLE 1

| Eu3+ | Dy3+ | Tb3+ | Sm3+ |
|---|---|---|---|
| 580 nm | 483 nm | 490 nm | 560 nm |
| 590 nm | 575 nm | 545 nm | 598 nm |
| 613 nm | 660 nm | 590 nm | 643 nm |
| 650 nm | | 620 nm | 710 nm |
| 690 nm | | 650 nm | |
| 710 nm | | | |

In an alternative embodiment, the interaction between the donor label and the acceptor label involves bioluminescence energy transfer (BRET). This differs from FRET in that the donor fluorophore of the FRET technique is replaced by a bioluminescent protein such as luciferase. In the presence of a substrate, bioluminescence from the bioluminescent protein excites the acceptor label by the same Förster resonance energy transfer mechanism as for FRET.

A criteria which should be considered in determining suitable pairings for BRET is the relative emission/fluorescence spectrum of the acceptor label compared to that of the bioluminescent protein. The emission spectrum of the bioluminescent protein should overlap with the absorbance spectrum of the acceptor protein such that the light energy from the bioluminescent protein luminescence emission is at a wavelength that is able to excite the acceptor label and thereby promote acceptor label fluorescence when the two molecules are in a proper proximity and orientation with respect to one another. Two common implementations of BRET that may be used comprise *Renilla* luciferase (RLuc) with either coelenterazine h (BRET$^1$; $\lambda_{em}$=~475 nm) or coelenterazine 400a (Clz400a) substrate (BRET$^2$; $\lambda_{em}$=~395 nm) as the donor system coupled to either of the GFP mutants, YFP (BRET$^1$; $\lambda_{em}$=~530 nm) or GFP$^2$ (BRET$^2$; $\lambda_{em}$=~510 nm). However, any suitable pairs of BRET donor and acceptor labels may be used that are known in the art, and as reviewed for example in Xia and Rao (*Curr Opin Biol* 20: 1-8, 2009).

*Renilla* luciferase/EGFP pairing has been compared to *Renilla* luciferase/EYEF pairing based on observable emission spectral peaks (Xu, 1999; Wang, et al (1997) in Bioluminescence and Chemiluminescence: Molecular Reporting with Photons, eds. Hastings et al (Wiley, New York), pp. 419-422). To study potential pairing, protein fusions are prepared containing the selected bioluminescent protein and acceptor molecule and are tested, in the presence of an appropriate substrate.

Preferably, the donor and acceptor labels are attached to the membrane protein at either the N-terminus or the C-terminus of the membrane protein. Labels attached to the termini are likely to have minimal effects on the structure and activity of the membrane protein. However, in principle, the labels can be placed in other regions of the membrane protein provided that they do not prevent folding of the membrane protein and/or interfere with its activity. Techniques to assess protein folding and activity to enable the skilled person to assess this are standard practice in the art.

It is preferred if the membrane proteins of the first and second populations are labelled with the donor and acceptor labels such that the labels are covalently attached to the membrane protein, for example at the N- or C-terminus of the membrane protein. For example, the membrane protein in the first population may be covalently attached to a donor label and the membrane protein in the second population may be covalently attached to an acceptor label, or the membrane protein in the first population may be covalently attached to an acceptor label and the membrane protein in the second population may be covalently attached to a donor label.

Techniques to covalently attach donor and acceptor labels to proteins are well known in the art, and any suitable method, including chemical conjugation, may be used.

For example, the Tag-Lite™ system, marketed by Cisbio may be used [7, 8, 9]. Here, the membrane protein of interest is cloned into an expression vector upstream or downstream of a SNAP or a CLIP tag. The SNAP and CLIP tags are related proteins that are modified forms of the mammalian O6-alkylguanine-DNA-alkyltransferase (AGT). The SNAP-tag and CLIP-tag substrates are derivates of benzyl purines and benzyl pyrimidines, where the benzyl group is attached to a functional group such as a fluorophore. During the labelling reaction, the modified benzyl group reacts with a free cysteine in AGT and the functional group is attached covalently. The expression of the membrane protein from this plasmid results in the production of a membrane protein having the SNAP or CLIP tag at the N-terminus or C-terminus. Membrane proteins can then be labeled with lanthanides (such as Terbium or Europium) that act as donor fluorophores. Thus, the membrane protein may be labelled with a donor or acceptor label (eg a donor or acceptor fluorophore) via a terminus tag, eg a C-terminal or N-terminal tag, such as the SNAP and CLIP tags using the Tag-Lite™ system. It will appreciated that for correct labelling of the C-terminus, the SNAP-tag or CLIP-tag substrate attached to the functional group (eg fluorophore) must be capable of crossing the cell membrane.

For donor and acceptor labels that are polypeptides (eg GFP), it will be understood that the labels may be covalently attached to the membrane protein by forming a fusion polypeptide. Preparation of fusion polypeptides is routine practice in the art and may involve chemical conjugation or may involve recombinant technology where the labelled membrane protein is expressed by a single polynucleotide.

In an alternative embodiment, the donor and acceptor labels may be attached to the membrane proteins non-covalently provided that the non-covalent interaction is strong enough to withstand the stability modulating agent and/or condition in step (b). Such non-covalent bindings may include immunological bindings or bindings such as via biotin/avidin or streptavidin. Whether the non-covalent interaction is sufficiently strong can be determined by exposing the labelled membrane protein to the stability modulating agent and/or condition and using an appropriate analytical technique to assess whether the label remains bound to the membrane protein following exposure.

It will be appreciated that the donor label or acceptor label may be attached to the membrane directly or indirectly. By 'attached to the membrane protein directly', we include the meaning of the label being either covalently or non-covalently attached to the membrane protein. By 'attached to the membrane protein indirectly', we include the meaning of the label being either covalently or non-covalently attached to a further moiety which, in turn, is covalently or non-covalently attached to the membrane protein.

Following exposure to the stability modulating agent and/or condition, the donor label is activated to permit a distance-dependent interaction with the acceptor label, and the level of aggregation assessed. By activating the donor label we include the meaning of initiating a process whereby there is a distance-dependent interaction between the donor and acceptor labels. The process may be one that results in the emission by the donor of a photon, or transfer of energy through resonance energy transfer or some other method.

Examples of donor activators include a photon (as in the case of a FRET donor) or a substrate of a bioluminescent protein (as in the case of a BRET donor). Thus, activating the donor label may comprise irradiating the donor label or exposing the donor label to a substance, so as to lead to a distance dependent interaction with the acceptor label.

In an embodiment, it may be desirable to also perform steps (a) and (c) of the method without performing step (b). This would provide an indication of background aggregation when the membrane protein is not exposed to a stability modulating agent and/or condition that can be compared to the level of aggregation when the membrane protein is exposed to a stability modulating agent and/or condition. In other words, the assay may be preceded by a step wherein the aggregation between membrane proteins of the first and second populations is assessed without exposure to a stability modulating agent and/or condition.

A second aspect of the invention provides an assay for assessing the conformational stability of a membrane protein, comprising:

(a) providing a sample comprising a membrane protein population, (b) exposing the membrane protein population to a stability modulating agent and/or condition, (c) labelling one of the N-terminus or C-terminus of the membrane protein with a donor label and the other of the N-terminus or C-terminus of the membrane protein with an acceptor label, (d) and assessing aggregation of the membrane proteins in the population by activating the donor label to permit a distance-dependent interaction with the acceptor label, which interaction produces a detectable signal.

In this assay, aggregation of the membrane protein is detected by virtue of the inability of the donor labels and acceptor labels to label the termini of the membrane protein when aggregated. When the membrane protein aggregates the labelling sites on the membrane protein become inaccessible and so the donor and acceptor labels cannot come into proximity with each other, and thereby cannot generate a detectable signal. If the membrane proteins are stable, there is less aggregation upon exposure to a destabilising agent and/or condition and so more signal, whereas if the membrane proteins are unstable, there is more aggregation upon exposure to a destabilising agent and/or condition and so less signal.

Preferences for the membrane protein population, donor label and acceptor label include those described above in relation to the first aspect of the invention.

Conveniently, one of the N-terminus or C-terminus of the membrane protein is capable of being labelled non-covalently with a donor label, and the other of the N-terminus or C-terminus of the membrane protein is capable of being labelled non-covalently with an acceptor label. Thus, the membrane protein may be engineered to contain a moiety at the N- and/or C-terminus that is capable of, either directly or indirectly, binding to the donor or acceptor label non-covalently. For example, the N-terminus and/or C-terminus may contain a tag, such as a c-Myc tag, recognised by an antibody that, in turn, is labelled with the donor label or acceptor label. Similarly, the N-terminus and/or C-terminus may contain a moiety that is recognised by one member of a binding partner pair (eg biotin and streptavidin/avidin), the other member of the binding partner pair, in turn, being labelled with the donor label or acceptor label. Example 1 illustrates this principle whereby a GPCR is N-terminally tagged with a biotin acceptor peptide (BAP) and is C-terminally tagged with a c-Myc tag. The GPCR may then be labelled by mixing with streptavidin labelled with d2 and anti-c-Myc antibody labelled with terbium. By labelling at the termini, the labels do not need to be capable of recognising the tertiary structure of the membrane protein, and so a loss of labelling is a direct measure of protein aggregation that is not skewed by changes in ligand or antibody binding sites that are not necessarily correlated with aggregation.

It is appreciated that one of the termini be labelled prior to step (b), provided that the labelling can withstand the stability modulating agent and/or condition.

Preferably the denaturant/denaturing condition is removed before labelling of one or both of the termini, so as to minimise adversely affecting the labelling procedure, as described further below.

Following exposure to the stability modulating agent and/or condition, the termini of the membrane protein are labelled. Either the N-terminus is labelled with a donor label and the C-terminus with an acceptor label, or the C-terminus is labelled with a donor label and the N-terminus with a donor label.

It is preferred if the amount of label that is added to the membrane protein is an amount that gives the maximal distance-dependent interaction signal while using the least amount of labelling reagents. The amount can be readily determined empirically and will generally depend on the choice of label and expression levels of membrane protein. Optimising the amount may involve doing a titration matrix of varying amounts of acceptor and donor labels, on a lysate containing the membrane protein of interest as well as a mock lysate. The optimal amount is one that gives the greatest difference in distance-dependent interaction signal (eg FRET signal) as between the lysate containing the membrane protein, and the mock lysate, while using the least amount of labelling reagents. The inventors have performed such an optimisation for streptavidin-d2 and Myc-Tb, and identified respective optimum concentrations of 1 nM and 100 nM.

Following activation of the donor label to permit a distance-dependent interaction with the acceptor label, the level of aggregation is then assessed.

In an embodiment, it may be desirable to also perform steps (a) and (c) of the method without performing step (b). This would provide an indication of background aggregation when the membrane protein is not exposed to a stability modulating agent and/or condition that can be compared to the level of aggregation when the membrane protein is exposed to a stability modulating agent and/or condition. In other words, the assay may be preceded by a step wherein the aggregation between membrane proteins of the first and second populations is assessed without exposure to a stability modulating agent and/or condition.

It will be appreciated that the invention also provides a membrane protein (eg GPCR) wherein one of the N-terminus or C-terminus is attached to a donor label (eg donor fluorophore) and the other of the N-terminus or C-terminus is attached to an acceptor label (eg acceptor fluorophore). Thus, any labelled membrane protein (eg GPCR) that is used in the assay of the second aspect of the invention is included in the scope of the invention. Preferences for the membrane proteins, donor label and acceptor label are as defined above. Thus, the membrane protein may be a GPCR that has the donor fluorophore (eg terbium) attached to the N-terminus and a donor fluorophore (eg EGFP) attached to the C-terminus. It will be understood that the attachment of the labels to the termini of the membrane protein need not be direct, but may be indirect, eg by virtue of the label being attached to a further moiety, such as a terminal tag, which in turn is attached to the membrane protein. It will also be understood that the labels may be attached non-covalently or covalently to the termini of the membrane protein. The invention also provides the use of such a membrane protein in an assay for measuring the conformational stability of the membrane protein.

The stability modulating agent and/or condition in the assays of the invention is preferably a denaturing agent and/or condition, for example one selected from one or more of heat, pH, a detergent, or a chaotropic agent. It will be appreciated that any denaturing agent and/or condition may be used which is known to modulate the secondary and tertiary structure of a protein but not the primary structure of a protein.

In relation to stability to heat (ie thermostability), it may be convenient to determine a "quasi $T_m$" or "quasi $T_{agg}$" ie the temperature at which 50% of the membrane protein (eg GPCR) is aggregated under stated conditions after incubation for a given period of time (eg 30 minutes). Mutant membrane proteins that have higher thermostability have an increased quasi Tm or Tagg compared to their parents.

In relation to stability to a detergent or to a chaotrope, typically the membrane protein is incubated for a defined time in the presence of a test detergent or a test chaotropic agent and the stability is determined using an assay of the invention.

In relation to an extreme of pH, a typical test pH would be chosen (eg in the range 4.5 to 5.5 (low pH) or in the range 8.5 to 9.5 (high pH).

Because relatively harsh detergents are used during crystallisation procedures, it is preferred that membrane proteins (eg GPCRs) are stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the membrane protein (eg GPCR) is more stable to any of $C_9$ maltoside or glucoside, $C_8$ maltoside or glucoside, LDAO and SDS, and so it is preferred that these detergents are used for stability testing.

It will be appreciated that heat is acting as the destabilising condition, and this can readily be removed by cooling the sample, for example by placing on ice. It is believed that thermostability may be a guide to the stability to other denaturing or destabilising agents and/or conditions. Thus, increased thermostability is likely to translate into stability in destabilising detergents, especially those that are more destabilising than DDM, eg those detergents with a smaller head group and a shorter alkyl chain and/or with a charged head group. We have found that a thermostable GPCR is also more stable towards harsh detergents, for example.

When an extreme of pH is used as the destabilising condition, it will be appreciated that this can be removed quickly by adding a neutralising agent. Similarly, when a chaotrope is used as a destabilizing agent, the destabilising effect can be removed by diluting the sample below the concentration in which the chaotrope exerts its chaotropic effect.

A considerable advantage of the assays of the invention is that they do not need to include a separation step to remove labelled ligand. This is an important difference from known methods of measuring membrane protein stability which involve use of a radiolabelled ligand. In such known methods, unbound radiolabel must be removed in a washing step prior to detection of the radiolabel. This separation step makes the known methods laborious and unsuitable for high throughput applications.

Although the assays of the invention do not use ligand binding as an indicator of the stability of a membrane protein, it may be beneficial to include a ligand of the membrane protein in the sample provided in step (a). The presence of a ligand, especially when the membrane protein is a GPCR, can improve stability and/or increase the probability of stabilising the GPCR in a desired conformation. Similarly, particular conformational states may be enriched for by varying physiochemical parameters or using additives such as any of pH, salt, metal ions, temperature, chaotropic agents, and glycerol. One may optimise physiochemical parameters to favour a particular conformation by doing standard pharmacological characterisations such as ligand binding affinities or functional assays under different parameters.

By "ligand" we include any molecule which binds to a membrane protein such as a GPCR.

When the membrane protein is a GPCR, the ligand will typically bind to one conformation of the GPCR (and may cause the GPCR to adopt this conformation), but does not bind as strongly to another conformation that the GPCR may be able to adopt. Thus, the presence of the ligand may be considered to encourage the GPCR to adopt the particular conformation. Preferably the ligand is from the agonist class of ligands and the particular conformation is an agonist conformation, or the ligand is from the antagonist class of ligands and the particular conformation is an antagonist conformation.

Many suitable ligands are known.

Typically, the ligand is a full agonist and is able to bind to the membrane protein (eg a receptor such as a GPCR) and is capable of eliciting a full (100%) biological response, measured for example by G-protein coupling, downstream signalling events or a physiological output such as vasodilation. Thus, typically, the biological response is GDP/GTP exchange in a G-protein, followed by stimulation of the linked effector pathway. The measurement, typically, is GDP/GTP exchange or a change in the level of the end product of the pathway (eg cAMP, cGMP or inositol phosphates). The ligand may also be a partial agonist and is able to bind to the GPCR and is capable of eliciting a partial (<100%) biological response.

The ligand may also be an inverse agonist, which is a molecule which binds to a membrane protein (eg a receptor such as a GPCR) and reduces its basal (ie unstimulated by agonist) activity sometimes even to zero.

The ligand may also be an antagonist, which is a molecule which binds to a membrane protein (eg a receptor such as a GPCR) and blocks binding of an agonist, so preventing a biological response. Inverse agonists and partial agonists may under certain assay conditions be antagonists.

The above ligands may be orthosteric, by which we include the meaning that they combine with the same site as the endogenous agonist; or they may be allosteric or allotopic, by which we include the meaning that they combine with a site distinct from the orthosteric site. The above ligands may be syntopic, by which we include the meaning that they interact with other ligand(s) at the same or an overlapping site. They may be reversible or irreversible.

In relation to antagonists, they may be surmountable, by which we include the meaning that the maximum effect of agonist is not reduced by either pre-treatment or simultaneous treatment with antagonist; or they may be insurmountable, by which we include the meaning that the maximum effect of agonist is reduced by either pre-treatment or simultaneous treatment with antagonist; or they may be neutral, by which we include the meaning the antagonist is one without inverse agonist or partial agonist activity. Antagonists typically are also inverse agonists.

Ligands for use in the invention may also be allosteric modulators such as positive allosteric modulators, potentiators, negative allosteric modulators and inhibitors. They may have activity as agonists or inverse agonists in their own right or they may only have activity in the presence of an agonist or inverse agonist in which case they are used in combination with such molecules in order to bind to the membrane protein (eg GPCR).

Neubig et al (2003) *Pharmacol. Rev.* 55, 597-606, incorporated herein by reference, describes various classes of ligands.

Preferably, the above-mentioned ligands are small organic or inorganic moieties, but they may be peptides or polypeptides. Typically, when the ligand is a small organic or inorganic moiety, it has a $M_r$ of from 50 to 2000, such as from 100 to 1000, for example from 100 to 500.

Typically, the ligand binds to the membrane protein (eg GPCR) with a $K_d$ of from mM to pM, such as in the range of from µM (micromolar) to nM. Generally, the ligands with the lowest Kd are preferred.

Small organic molecule ligands are well known in the art. Other small molecule ligands include 5HT which is a full agonist at the 5HT1A receptor; eltoprazine which is a partial agonist at the 5HT1A receptor (see Newman-Tancredi et al (1997) *Neurophamacology* 36, 451-459); (+)-butaclamol and spiperone are dopamine D2 receptor inverse agonists (see Roberts & Strange (2005) *Br. J. Pharmacol.* 145, 34-42); and WIN55212-3 is a neutral antagonist of CB2 (Savinainen et al (2005) *Br. J. Pharmacol.* 145, 636-645).

The ligand may be a peptidomimetic, a nucleic acid, a peptide nucleic acid (PNA) or an aptamer. It may be an ion such as $Na^+$ or $Zn^{2+}$, a lipid such as oleamide, or a carbohydrate such as heparin.

The ligand may be a polypeptide which binds to the membrane protein (eg receptor such as a GPCR). Such polypeptides (by which we include oligopeptides) are typically from $M_r$ 500 to $M_r$ 50,000, but may be larger. The polypeptide may be a naturally occurring GPCR-interacting protein or other protein which interacts with the GPCR, or a derivative or fragment thereof, provided that it binds selectively to the GPCR in a particular conformation. GPCR-interacting proteins include those associated with signalling and those associated with trafficking, which often act via PDZ domains in the C terminal portion of the GPCR.

Polypeptides which are known to bind certain GPCRs include any of a G protein, an arrestin, a RGS protein, G protein receptor kinase, a RAMP, a 14-3-3 protein, a NSF, a periplakin, a spinophilin, a GPCR kinase, a receptor tyrosine kinase, an ion channel or subunit thereof, an ankyrin and a Shanks or Homer protein. Other polypeptides include NMDA receptor subunits NR1 or NR2a, calcyon, or a fibronectin domain framework. The polypeptide may be one which binds to an extracellular domain of a GPCR, such as fibulin-1. The polypeptide may be another GPCR, which binds to the selected GPCR in a hetero-oligomer. A review of protein-protein interactions at GPCRs is found in Milligan & White (2001) *Trends Pharmacol. Sci.* 22, 513-518, or in Bockaert et al (2004) *Curr. Opinion Drug Discov. Dev.* 7, 649-657 incorporated herein by reference.

The polypeptide ligand may conveniently be an antibody which binds to the membrane protein (eg GPCR). By the term "antibody" we include naturally-occurring antibodies, monoclonal antibodies and fragments thereof. We also include engineered antibodies and molecules which are antibody-like in their binding characteristics, including single chain Fv (scFv) molecules and domain antibodies (dAbs). Mention is also made of camelid antibodies and engineered camelid antibodies. Such molecules which bind GPCRs are known in the art and in any event can be made using well known technology. Suitable antibodies include ones presently used in radioimmunoassay (RIAs) for GPCRs since they tend to recognise conformational epitopes.

The polypeptide may also be a binding protein based on a modular framework, such as ankyrin repeat proteins, armadillo repeat proteins, leucine rich proteins, tetratriopeptide repeat proteins or Designed Ankyrin Repeat Proteins (DARPins) or proteins based on lipocalin or fibronectin domains or Affilin scaffolds based on either human gamma crystalline or human ubiquitin.

It will be appreciated that the use of antibodies, or other "universal" binding polypeptides (such as G-proteins which are known to couple with many different GPCRs) may be particularly advantageous in the use of the method on "orphan" GPCRs for which the natural ligand, and small molecule ligands, are not known.

It will be appreciated that the above assays may be used in methods to select membrane proteins (eg GPCRs) with increased conformational stability. Such methods have the advantage over existing methods that there is no need for a separation step to remove labelled ligand. Also, the method can be performed even where a good radioligand with high affinity and/or favourable properties in detergent is not available.

Accordingly, a third aspect of the invention provides a method for selecting a membrane protein (eg GPCR) with increased conformational stability, comprising:

(a) comparing the conformational stability of one or more mutants of a parent membrane proteins with the conformational stability of the parent membrane protein according to the assay of the first or second aspects of the invention, and (b) selecting one or more mutants that have increased conformational stability relative to the parent membrane protein.

By including a ligand in either assay of the invention as described above, the method of the third aspect of the invention may be considered to be a way of selecting membrane proteins (eg GPCRs) which are trapped in a conformation of biological relevance (eg ligand bound state), and which are more stable with respect to that conformation. Preferably, the ligand is from the agonist class of ligands and the particular conformation is an agonist conformation, or the ligand is from the antagonist class of ligands and the particular conformation is an antagonist conformation.

The mutant membrane proteins (eg GPCRs) may be prepared by any suitable method. Conveniently, the mutant protein is encoded by a suitable nucleic acid molecule and is expressed in a suitable host cell. The preparation of suitable nucleic acid molecules, expression systems and host cells include those described above.

In a particular embodiment of the invention, the membrane protein is CCR5, the donor label is terbium and the acceptor label is EGFP. Terbium may be attached to the N-terminus by using SNAP tag technology. EGFP may be attached to the C-terminus by being expressed as a C-terminal fusion.

In a further preferred embodiment of the invention, the membrane protein is CCR5, the donor label is terbium and the acceptor label is d2. Terbium may be non-covalently attached to the C-terminus via labelling an anti-c-Myc antibody that is bound to a c-Myc epitope at the C-terminus. d2 may be non-covalently attached to the N-terminus via labelling streptavidin that is bound to biotin which in turn binds biotin acceptor peptide (BAP) fused to the N-terminus.

In a particular embodiment of the invention, the membrane protein is a GPCR such as any of GLP1R, CMKLR, or TGR5 (GPBAR-I), the donor label is terbium and the acceptor label is EGFP. Terbium may be attached to the N-terminus by using SNAP tag technology. EGFP may be attached to the C-terminus by being expressed as a C-terminal fusion.

In a further preferred embodiment of the invention, the membrane protein is a GPCR such as any of GLP1R, CMKLR, or TGR5 (GPBAR-I), the donor label is terbium and the acceptor label is d2. Terbium may be non-covalently attached to the C-terminus via labelling an anti-c-Myc antibody that is bound to a c-Myc epitope at the C-terminus. d2 may be non-covalently attached to the N-terminus via labelling streptavidin that is bound to biotin which in turn binds biotin acceptor peptide (BAP) fused to the N-terminus.

The invention will now be described with the aid of the following Figures and Examples:

FIG. 1: (a) Principle of the intermolecular aggregation assay. Terbium labelled or EGFP-tagged receptors are solubilised and purified. The 1:1 mixed samples are heated and FRET is measured. (b) An example of receptor stabilities measured using this assay, the values denote Tagg.

Figure 2:
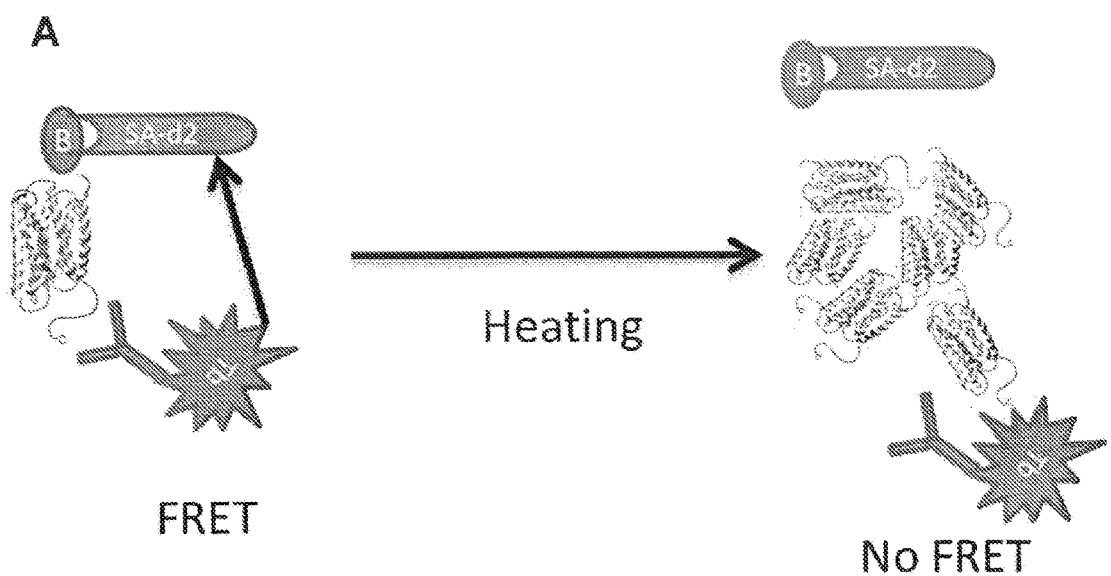
Figure 2:
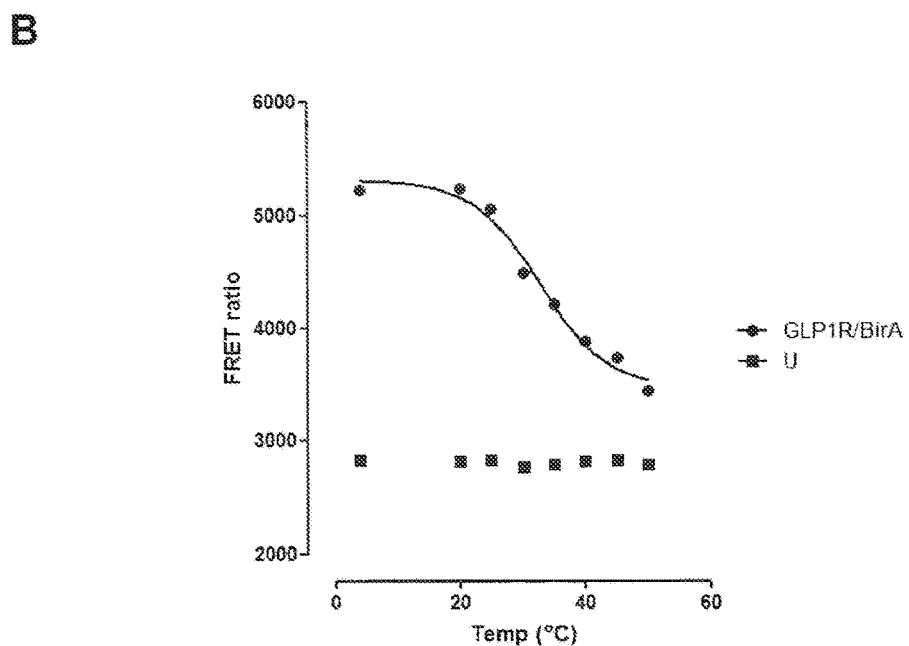

FIG. 2: (a) Principle of the intramolecular aggregation assay. In vivo biotinylated receptors are solubilised and incubated at different temperatures. The lysates are then mixed with d2 labelled streptavidin and terbium labelled anti-cMyc antibody and FRET is measured. Upon heat induced aggregation, the levels of FRET are reduced due to the inaccessibility of the sites to label the receptor. (b) An example of receptor stabilities measured using this assay, the values denote Tagg. U represents the FRET values measured in lysates prepared from mock transfected cells. FRET ratio represents emission at 650 nm normalised to the emission at 620 nm.

Figure 3:
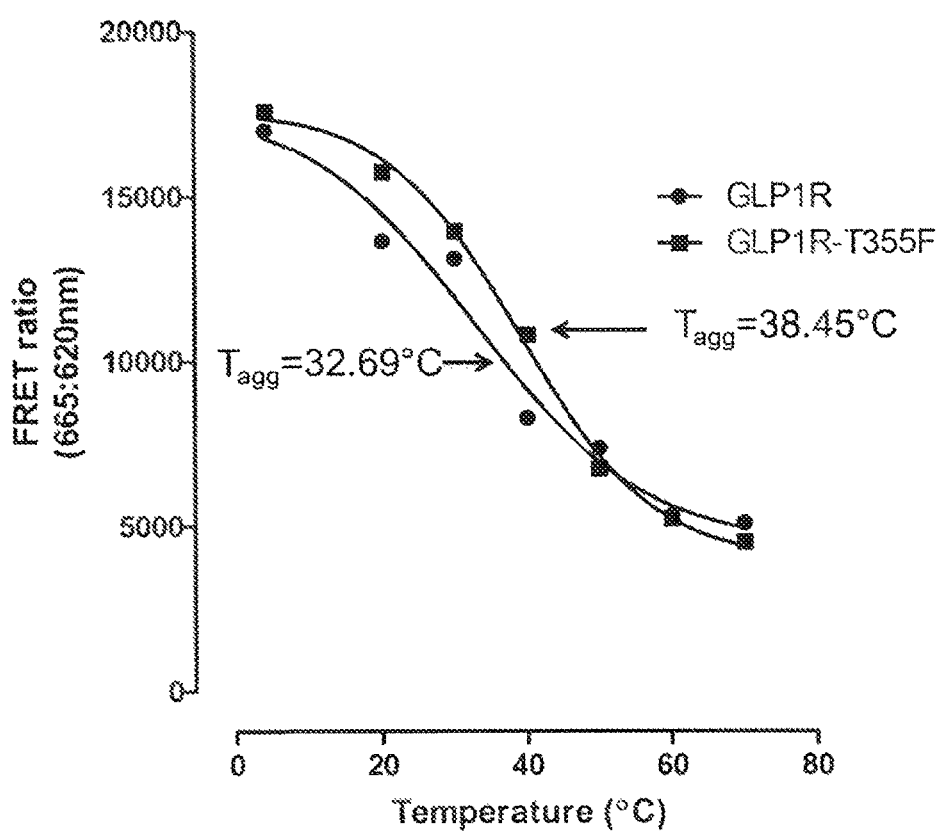

FIG. 3: Stability of wild-type and mutant (T355F) GLP1R measured using intramolecular aggregation assay. Wild-type and T355F GLP1R constructs (both N-terminally BAP tagged and C-terminally c-Myc tagged) were co-expressed in HEK293T cells with BirA. Following solubilisation in 1% DDM, samples were incubated at different temperatures for 30 minutes. FRET was measured after addition of d2 labelled streptavidin and terbium labelled anti-cMyc antibody.

EXAMPLE 1: METHODOLOGY FOR RECEPTOR STABILISATION

Our conventional method for receptor stabilisation uses ligand binding to measure the levels of active receptor. Briefly, solubilised receptors that have been incubated with a radio-labelled ligand are heated at different temperatures for a set amount of time. Next, the excess and unbound ligand is separated from the receptor bound ligand and the residual level of radioactivity is measured. Plotting this data against temperature gives a thermal decay curve and the Tm value is defined as the temperature at which 50% of receptor activity is retained. Obviously this method relies on the availability of a good radioligand with high affinity and favourable properties in detergent. There has therefore been a need to develop new methodologies that would allow us to stabilise receptors in cases where such a ligand is not available. We refer to these methodologies as ligand-independent methods which means that ligand binding ability of the receptor is not used to measure receptor activity, although, the ligand can be present to increase stability or increase the probability of stabilising the receptor in the desired conformation.

Intermolecular Aggregation Assay

Protein aggregation upon unfolding is a general feature of all proteins that occurs to varying degrees in different proteins. Membrane proteins are known to exhibit high levels of aggregation after solubilisation and more so after denaturation. It is therefore possible to use the levels of aggregation as a measure of global stability.

An assay that allows aggregation to be measured in an easy and miniaturisable format would be a useful tool to generate a stable receptor. There are a number of different ways that aggregation could be measured including the biophysical methods described above. Most of these methods require high amounts of very pure protein.

We have developed a method that allows receptor aggregation to be measured from small amounts of semi-purified preparations. In order to measure the receptor aggregation using this assay, two populations of the receptor are labelled with either a FRET acceptor group or a FRET donor group (FIG. 1a). We have used the SNAP tag technology to label the receptors N-terminally with terbium that acts as the FRET donor. The FRET acceptor is EGFP that is expressed as a C-terminal fusion. These two populations of the receptor are expressed, solubilised and partially purified separately. The semi-pure preps of the two sets are mixed in a 1:1 ratio and the mixture is incubated at different temperatures for a set amount of time. As the receptors unfold and aggregates are formed, FRET acceptor and donor are brought in close proximity that results in FRET emission. Increase in FRET is plotted against temperature and the temperature at which 50% FRET is observed is defined as $T_{agg}$ (FIG. 1b).

Intramolecular Aggregation Assay

This assay is a variation on the previous method. In this assay, the FRET acceptor and donor are placed on the N- and C-termini of the same receptor molecule. However, importantly, the receptor is solubilised and heated prior to labelling with the FRET acceptor and donor. So, as the receptor unfolds and aggregates the sites of FRET acceptor and donor labelling are obscured and thus become inaccessible. This in turn results in loss of FRET as a function of temperature and the $T_{agg}$ is defined as the temperature at which 50% FRET is observed (FIG. 2a). In this example, the receptor is tagged N-terminally with a biotin acceptor peptide (BAP) and is C-terminally tagged with cMyc tag. The receptor is co-expressed with biotin ligase A (BirA) enzyme which leads to the expression of an N-terminally biotinylated receptor. Following solubilisation, the crude lysate is incubated at different temperatures for a set amount of time. The lysates are then mixed with streptavidin labelled with d2 and anti-cMyc antibody labelled with terbium. The levels of FRET are then measured and plotted against temperature (FIG. 2b).

In order to see if this method was capable of identifying thermostabilisng mutations, a number of mutants were generated in the plasmid encoding GLP1R using site directed mutagenesis. The intramolecular aggregation assay was then used to assess the thermal stability of the mutants compared to wild-type GLP1R. FIG. 3 shows exemplary data for T355F mutation that confers ~6° C. increase in thermal stability of GLP1R. As seen from the figure, the value of Tagg for the stabilised mutant GLP1R is higher than that of the wild-type GLP1R.

Materials and Methods

Receptor Expression

In all cases described, the receptors were expressed transiently in HEK293T cells. Briefly, cells were seeded at the density of 3×10⁶ cells in 10 cm petri dishes containing Dulbecco's Modified Eagle Medium (DMEM) supplemented with 10% foetal bovine serum (FBS) and incubated overnight in 37° C. incubator. The next day, cells were transfected using 6 ug of plasmid encoding the receptor of interest using GeneJuice according to the manufacturer's instructions. Cells were incubated for about 40 hours post-transfection at the 37° C. incubator.

Receptor Solubilisation

Following transfection cells were harvested in phosphate buffered saline and washed once in the same buffer. Cells were then solubilised in total 1 mL of solubilisation buffer containing 50 mM 4-(2-hydroxyethyl)-1-piperazineethanesulfonic acid (HEPES) and 150 mM sodium chloride adjusted to pH 7.5, supplemented with 1% n-Dodecyl-R-maltoside (DDM) and protease inhibitor cocktail. Receptors were solubilised for 1 hour with end-to-end rotation. All solubilisation steps as well as the subsequent steps were carried out at 4° C.

Intermolecular Aggregation Assay

SNAP-tagged and EGFP-tagged receptors were expressed separately in HEK293T cells as described above. Prior to solubilisation, SNAP-tagged receptors were harvested and re-suspended in DMEM plus FBS containing 250 nM of SNAP-Lumi4Tb (Cisbio) and incubated for 1 hour at 37° C. incubator to label the N-terminus. Cells were then washed three times with 1 mL of PBS to remove the excess unbound SNAP-Lumi4Tb. After the last wash cells were solubilised in parallel along with cells expressing EGFP tagged receptor in 1% DDM. The crude lysates were clarified by centrifugation at 13000 rpm for 10 minutes at 4° C. The cleared lysates were incubated with 250 uL of 50% slurry Ni-NTA agarose resin pre-equilibrated in the solubilisation buffer in order to purify receptors using the C-terminal 10× His tag. The mixture was incubated at 4° C. with end-to-end rotation for 1.5 hour and then washed 3× with 1 mL of chilled wash buffer containing 50 mM HEPES, 150 mM NaCl, 0.03% DDM, 20 mM Imidazole, pH adjusted to 7.5. After the last wash receptors were eluted in 500 uL of elution buffer containing 50 mM HEPES, 150 mM NaCl, 0.03% DDM and 100 mM Histidine, pH adjusted to 7.5. The Lumi4Tb tagged and EGFP tagged samples were mixed 1:1 and aliquots were incubated at increasing temperatures for 30 minutes. The samples were then returned to 4° C. and transferred to white 96-well plates and FRET was measured between Lumi4Tb and EGFP using PHERAstar Plus (BMG Labtech) instrument. The FRET settings were according to the recommendations of the manufacturer.

Intramolecular Aggregation Assay

Receptors tagged N-terminally with the biotin acceptor tag (BAP) and C-terminally with c-Myc tag were expressed transiently in HEK293T cells as described above. It is notable that the plasmid also encodes for the BirA enzyme that mediates biotinylation on the BAP tag. Cells were incubated with 100 uM of biotin during expression. Following harvesting and solubilisation, aliquots of cleared lysates were incubated at increasing temperatures for 30 minutes. Samples were cooled to 4° C. and 20 uL of each sample was added to 20 uL of FRET mixture pre-aliquoted in white 384 well plate containing 2 nM anti-cMyc antibody conjugated to terbium (Cisbio) and 200 nM Streptavidin conjugated to d2 fluorophore (Cisbio). The plate was incubated overnight at 4° C. before measuring the FRET signal on PHERAstar Plus according to the recommendations of the manufacturer.

TABLE A

| Official IUPHAR name | Human gene name | Rat gene name | Mouse gene name |
|---|---|---|---|
| 5HT1a | HTR1A | Htr1a | Htr1a |
| 5HT2A | HTR2A | Htr2a | Htr2a |
| 5HT2C | HTR2C | Htr2c | Htr2c |
| 5HT6 | HTR6 | Htr6 | Htr6 |
| 5HT7 | HTR7 | Htr7 | Htr7 |
| M1 | CHRM1 | Chrm1 | Chrm1 |
| M2 | CHRM2 | Chrm2 | Chrm2 |
| M3 | CHRM3 | Chrm3 | Chrm3 |
| M4 | CHRM4 | Chrm4 | Chrm4 |
| M5 | CHRM5 | Chrm5 | Chrm5 |
| C3a | C3AR1 | C3ar1 | C3ar1 |
| C5a | C5R1 | C5r1 | C5r1 |
| C5L2 | GPR77 | Gpr77 | Gpr77 |
| AT1 | AGTR1 | Agtr1b | Agtr1b |
| APJ | AGTRL1 | Agtrl1 | Agtrl1 |
| GPBA | GPBAR1 | Gpbar1 | Gpbar1 |
| BB1 | NMBR | Nmbr | Nmbr |
| BB2 | GRPR | Grpr | Grpr |
| BB3 | BRS3 | Brs3 | Brs3 |
| BK1 | BDKRB1 | Bdkrb1 | Bdkrb1 |
| BK2 | BDKRB2 | Bdkrb2 | Bdkrb2 |
| CB1 | CNR1 | Cnr1 | Cnr1 |
| CB2 | CNR2 | Cnr2 | Cnr2 |
| CCR1 | CCR1 | Ccr1 | Ccr1 |
| CCR2 | CCR2 | Ccr2 | Ccr2 |
| CCR3 | CCR3 | Ccr3 | Ccr3 |
| CCR4 | CCR4 | Ccr4 | Ccr4 |
| CCR5 | CCR5 | Ccr5 | Ccr5 |
| CCR6 | CCR6 | Ccr6 | Ccr6 |
| CCR7 | CCR7 | Ccr7 | Ccr7 |
| CCR8 | CCR8 | Ccr8 | Ccr8 |
| CCR9 | CCR9 | Ccr9 | Ccr9 |
| CCR10 | CCR10 | Gpr2 | Gpr2 |
| CXCR1 | IL8RA | Il8ra | Il8ra |
| CXCR2 | IL8RB | Il8rb | Il8rb |
| CXCR3 | CXCR3 | Cxcr3 | Cxcr3 |
| CXCR4 | CXCR4 | Cxcr4 | Cxcr4 |
| CXCR5 | CXCR5 | Blr1 | Blr1 |
| CXCR6 | CXCR6 | Cxcr6 | Cxcr6 |
| CX3CR1 | CX3CR1 | Cx3cr1 | Cx3cr1 |
| XCR1 | XCR1 | Xcr1 | Xcr1 |
| DRD1 | DRD1 | Drd1a | Drd1a |
| DRD2 | DRD2 | Drd2 | Drd2 |
| DRD3 | DRD3 | Drd3 | Drd3 |
| DRD4 | DRD4 | Drd4 | Drd4 |
| DRD5 | DRD5 | Drd5 | Drd5 |
| GPER | GPER | Gpr30 | Gper |
| FPR1 | FPR1 | Fpr1 | Fpr1 |
| FPR2/ALX | FPR2 | Fpr2 | Fpr2 |
| FPR3 | FPR3 | Fpr3 | Fpr3 |
| FFA1 | FFAR1 | Ffar1 | Ffar1 |
| FFA2 | FFAR2 | Gpr43 | Ffar2 |
| FFA3 | FFAR3 | Ffar3 | Ffar3 |
| GALR1 | GALR1 | Galr1 | Galr1 |
| GALR2 | GALR2 | Galr2 | Galr2 |
| GALR3 | GALR3 | Galr3 | Galr3 |
| ghrelin | GHSR | Ghsr | Ghsr |
| FSH | FSHR | Fshr | Fshr |
| LH | LHCGR | Lhcgr | Lhcgr |
| GnRH | GNRHR | Gnrhr | Gnrhr |
| GnRH2 | GNRHR2 | | |
| KiSS1 | KISS1R | Kiss1r | Kiss1r |
| OXE | OXER1 | | |
| FPR2/ALX | FPR2 | Fpr2 | Fpr2 |
| LPAR1 | LPAR1 | Lpar1 | Lpar1 |
| LPAR2 | LPAR2 | Lpar2 | Lpar2 |
| LPAR3 | LPAR3 | Lpar3 | Lpar3 |
| S1PR1 | S1PR1 | S1pr1 | S1pr1 |
| S1PR2 | S1PR2 | S1pr2 | S1pr2 |
| S1PR3 | S1PR3 | S1pr3 | S1pr3 |
| S1PR4 | S1PR4 | S1pr4 | S1pr4 |
| S1PR5 | S1PR5 | S1pr5 | S1pr5 |

TABLE A-continued

| Official IUPHAR name | Human gene name | Rat gene name | Mouse gene name |
|---|---|---|---|
| MCHR1 | MCHR1 | Mchr1 | Mchr1 |
| MCHR2 | MCHR2 | | |
| MC1R | MC1R | Mc1r | Mc1r |
| MC2R | MC2R | Mc2r | Mc2r |
| MC3R | MC3R | Mc3r | Mc3r |
| MC4R | MC4R | Mc4r | Mc4r |
| MC5R | MC5R | Mc5r | Mc5r |
| MTNR1A | MTNR1A | Mtnr1a | Mtnr1a |
| MTNR1B | MTNR1B | Mtnr1b | Mtnr1b |
| NMU1 | NMUR1 | Nmur1 | Nmur1 |
| NMU2 | NMUR2 | Nmur2 | Nmur2 |
| NPFF1 | NPFFR1 | Npffr1 | |
| NPFF2 | NPFFR2 | Npffr2 | Npffr2 |
| NPS | NPSR1 | Npsr1 | Npsr1 |
| NPBW1 | NPBWR1 | Npbwr1 | Npbwr1 |
| NPBW2 | NPBWR2 | | |
| NPY1 | NPY1R | Npy1r | Npy1r |
| NPY2R | NPY2R | Npy2r | Npy2r |
| PPYR1 | PPYR1 | Ppyr1 | Ppyr1 |
| NPY5R | NPY5R | Npy5r | Npy5r |
| NTSR1 | NTSR1 | Ntsr | Ntsr |
| NTSR2 | NTSR2 | Ntsr2 | Ntsr2 |
| GPR81 (temporary name) | GPR81 | Gpr81 | Gpr81 |
| GPR109A (temporary name) | GPR109A | Gpr109a | Gpr109a |
| GPR109B (temporary name) | GPR109B | | |
| Delta | OPRD1 | Oprd1 | Oprd1 |
| Kappa | OPRK1 | Oprk1 | Oprk1 |
| Mu | OPRM1 | Oprm1 | Oprm1 |
| NOP | OPRL1 | Oprl | Oprl1 |
| OX1 | HCRTR1 | Hcrtr1 | Hcrtr1 |
| OX2 | HCRTR2 | Hcrtr2 | Hcrtr2 |
| P2RY2 | P2RY2 | P2ry2 | P2ry2 |
| P2RY11 | P2RY11 | | |
| P2RY12 | P2RY12 | P2ry12 | P2ry12 |
| PROKR1 | PROKR1 | Prokr1 | Prokr1 |
| PROKR2 | PROKR2 | Prokr2 | Prokr2 |
| PRRP | PRLHR | Prlhr | Prlhr |
| PAR1 | F2R | F2r | F2r |
| PAR2 | F2RL1 | F2rl1 | F2rl1 |
| RXFP1 | RXFP1 | Rxfp1 | Rxfp1 |
| RXFP2 | RXFP2 | Rxfp2 | Rxfp2 |
| RXFP3 | RXFP3 | Rxfp3 | Rxfp3 |
| RXFP4 | RXFP4 | | Rxfp4 |
| SSTR1 | SSTR1 | Sstr1 | Sstr1 |
| SSTR2 | SSTR2 | Sstr2 | Sstr2 |
| SSTR5 | SSTR5 | Sstr5 | Sstr5 |
| V1A | AVPR1A | Avpr1a | Avpr1a |
| V1B | AVPR1B | Avpr1b | Avpr1b |
| V2 | AVPR2 | Avpr2 | Avpr2 |
| CCRL2 | CCRL2 | Ccrl2 | Ccrl2 |
| CMKLR1 | CMKLR1 | Cmklr1 | Cmklr1 |
| CMKOR1 | CMKOR1 | Rdc1 | Cmkor1 |
| CT | CALCR | Calcr | Calcr |
| CALCRL | CALCRL | Calcrl | Calcrl |
| CRF1 | CRHR1 | Crhr1 | Crhr1 |
| CRF2 | CRHR2 | Crhr2 | Crhr2 |
| GHRH | GHRHR | Ghrhr | Ghrhr |
| GIP | GIPR | Gipr | Gipr |
| GLP-1 | GLP1R | Glp1r | Glp1r |
| GLP-2 | GLP2R | Glp2r | Glp2r |
| glucagon | GCGR | Gcgr | Gcgr |
| secretin | SCTR | Sctr | Sctr |
| PTH1 | PTH1R | Pth1r | Pth1r |
| PTH2 | PTHR2 | Pthr2 | Pthr2 |
| PAC1 | ADCYAP1R1 | Adcyap1r1 | Adcyap1r1 |
| VPAC1 | VIPR1 | Vipr1 | Vipr1 |
| VPAC2 | VIPR2 | Vipr2 | Vipr2 |
| CaS | CASR | Casr | Casr |
| GABBR1 | GABBR1 | Gabbr1 | Gabbr1 |
| GABBR2 | GABBR2 | Gabbr2 | Gabbr2 |
| mGluR1 | GRM1 | Grm1 | Grm1 |
| mGluR2 | GRM2 | Grm2 | Grm2 |
| mGluR3 | GRM3 | Grm3 | Grm3 |
| mGluR4 | GRM4 | Grm4 | Grm4 |
| mGluR5 | GRM5 | Grm5 | Grm5 |
| mGluR6 | GRM6 | Grm6 | Grm6 |
| mGluR7 | GRM7 | Grm7 | Grm7 |
| mGluR8 | GRM8 | Grm8 | Grm8 |

TABLE B

| Official IUPHAR receptor name | Human gene name | Rat gene name | Mouse gene name |
|---|---|---|---|
| CCRL2 | CCRL2 | Ccrl2 | Ccrl2 |
| CMKLR1 | CMKLR1 | Cmklr1 | Cmklr1 |
| CMKOR1 | CMKOR1 | Rdc1 | Cmkor1 |
| EBI2 | GPR183 | Gpr183 | Gpr183 |
| GPR1 | GPR1 | Gpr1 | Gpr1 |
| GPR3 | GPR3 | Gpr3 | Gpr3 |
| GPR4 | GPR4 | Gpr4 | Gpr4 |
| GPR6 | GPR6 | Gpr6 | Gpr6 |
| GPR12 | GPR12 | Gpcr12 | Gpr12 |
| GPR15 | GPR15 | Gpr15 | Gpr15 |
| GPR17 | GPR17 | Gpr17 | Gpr17 |
| GPR18 | GPR18 | Gpr18 | Gpr18 |
| GPR19 | GPR19 | Gpr19 | Gpr19 |
| GPR20 | GPR20 | Gpr20 | Gpr20 |
| GPR21 | GPR21 | Gpr21 | Gpr21 |
| GPR22 | GPR22 | Gpr22 | Gpr22 |
| GPR23 | GPR23 | Gpr23_predicted | Gpr23 |
| GPR25 | GPR25 | Gpr25 | Gpr25 |
| GPR26 | GPR26 | Gpr26 | Gpr26 |
| GPR27 | GPR27 | Gpr27 | Gpr27 |
| GPR31 | GPR31 | Gpr31 | Gpr31c |
| GPR32 | GPR32 | | |
| GPR34 | GPR34 | GPR34 | Gpr34 |
| GPR35 | GPR35 | Gpr35 | Gpr35 |
| GPR37 | GPR37 | Gpr37 | Gpr37 |
| GPR37L1 | GPR37L1 | Gpr37l1 | Gpr37l1 |
| GPR39 | GPR39 | Gpr39 | Gpr39 |
| GPR45 | GPR45 | Gpr45 | Gpr45 |
| GPR50 | GPR50 | Gpr50 | Gpr50 |
| GPR52 | GPR52 | Gpr52 | Gpr52 |
| GPR55 | GPR55 | | Gpr55 |
| GPR61 | GPR61 | Gpr61 | Gpr61 |
| GPR62 | GPR62 | RGD1560166 | Gpr62 |
| GPR63 | GPR63 | Gpr63 | Gpr63 |
| GPR65 | GPR65 | Gpr65 | Gpr65 |
| GPR68 | GPR68 | Gpr68 | Gpr68 |
| GPR75 | GPR75 | Gpr75 | Gpr75 |
| GPR78 | GPR78 | | |
| GPR82 | GPR82 | | Gpr82 |
| GPR83 | GPR83 | Gpr83 | Gpr83 |
| GPR84 | GPR84 | Gpr84 | Gpr84 |
| GPR85 | GPR85 | Gpr85 | Gpr85 |
| GPR87 | GPR87 | Gpr87 | Gpr87 |
| GPR88 | GPR88 | Gpr88 | Gpr88 |
| GPR92 | GPR92 | RGD1562580_predicted | Gpr92 |
| GPR101 | GPR101 | Gpr101 | Gpr101 |
| GPR119 | GPR119 | Gpr119 | Gpr119 |
| GPR120 | GPR120 | Gpr120 | Gpr120 |
| GPR132 | GPR132 | Gpr132 | Gpr132 |
| GPR135 | GPR135 | Gpr135 | Gpr135 |
| GPR139 | GPR139 | Gpr139 | Gpr139 |
| GPR141 | GPR141 | Gpr141 | Gpr141 |
| GPR142 | GPR142 | Gpr142 | Gpr142 |
| GPR146 | GPR146 | Gpr146 | Gpr146 |
| GPR148 | GPR148 | | |
| GPR149 | GPR149 | | Gpr149 |
| GPR150 | GPR150 | Gpr150 | Gpr150 |
| GPR151 | GPR151 | Gpr151 | Gpr151 |
| GPR152 | GPR152 | Gpr152 | Gpr152 |
| GPR153 | GPR153 | Gpr153 | Gpr153 |
| GPR160 | GPR160 | Gpr160 | Gpr160 |

TABLE B-continued

| Official IUPHAR receptor name | Human gene name | Rat gene name | Mouse gene name |
| --- | --- | --- | --- |
| GPR161 | GPR161 | RGD1563245 | Gpr161 |
| GPR162 | GPR162 | Gpr162 | Gpr162 |
| GPR171 | GPR171 | Gpr171 | Gpr171 |
| GPR173 | GPR173 | Gpr173 | Gpr173 |
| GPR174 | GPR174 | Gpr174 | Gpr174 |
| GPR182 | GPR182 | Gpr182 | Gpr182 |
| LGR4 | LGR4 | Lgr4 | Lgr4 |
| LGR5 | LGR5 | Lgr5 | Lgr5 |
| LGR6 | LGR6 | Lgr6 | Lgr6 |
| MAS1 | MAS1 | Mas1 | Mas1 |
| MAS1L | MAS1L | | |
| MRGPRD | MRGPRD | Mrgprd | Mrgprd |
| MRGPRE | MRGPRE | Mrgpre | Mrgpre |
| MRGPRF | MRGPRF | Mrgprf | Mrgprf |
| MRGPRG | MRGPRG | Mrgprg | Mrgprg |
| MRGPRX1 | MRGPRX1 | Mrgprx1 | Mrgprx1 |
| MRGPRX2 | MRGPRX2 | Mrgprx2 | Mrgprx2 |
| MRGPRX3 | MRGPRX3 | Mrga10 | Mrgpra9 |
| MRGPRX4 | MRGPRX4 | | |
| OPN3 | OPN3 | Opn3 | Opn3 |
| OPN5 | OPN5 | Opn5 | Opn5 |
| OXGR1 | OXGR1 | Oxgr1 | Oxgr1 |
| P2RY5 | P2RY5 | P2ry5 | P2y5 |
| P2RY8 | P2RY8 | | |
| P2RY10 | P2RY10 | P2ry10 | P2ry10 |
| SUCNR1 | SUCNR1 | Sucnr1 | Sucnr1 |
| TAAR2 | TAAR2 | Taar2 | Taar2 |
| TAAR5 | TAAR5 | Taar5 | Taar5 |
| TAAR6 | TAAR6 | Taar6 | Taar6 |
| TAAR8 | TAAR8 | Taar8a | Taar8b |
| TAAR9 | TAAR9 | Taar9 | Taar9 |
| BAI1 | BAI1 | Bai1 | Bai1 |
| BAI2 | BAI2 | Bai2 | Bai2 |
| BAI3 | BAI3 | Bai3 | Bai3 |
| CD97 | CD97 | cd97 | Cd97 |
| CELSR1 | CELSR1 | Celsr1 | Celsr1 |
| CELSR2 | CELSR2 | Celsr2 | Celsr2 |
| CELSR3 | CELSR3 | Celsr3 | Celsr3 |
| ELTD1 | ELTD1 | Eltd1 | Eltd1 |
| EMR1 | EMR1 | Emr1 | Emr1 |
| EMR2 | EMR2 | | |
| EMR3 | EMR3 | | |
| GPR56 | GPR56 | Gpr56 | Gpr56 |
| GPR64 | GPR64 | Gpr64 | Gpr64 |
| GPR97 | GPR97 | Gpr97 | Gpr97 |
| GPR98 | GPR98 | Gpr98 | Gpr98 |
| GPR110 | GPR110 | Gpr110 | Gpr110 |
| GPR111 | GPR111 | | Gpr111 |
| GPR112 | GPR112 | Gpr112 | Gpr112 |
| GPR113 | GPR113 | Gpr113 | Gpr113 |
| GPR114 | GPR114 | Gpr114 | Gpr114 |
| GPR115 | GPR115 | Gpr115 | Gpr115 |
| GPR116 | GPR116 | Gpr116 | Gpr116 |
| GPR123 | GPR123 | Gpr123 | Gpr123 |
| GPR124 | GPR124 | Gpr124 | Gpr124 |
| GPR125 | GPR125 | Gpr125 | Gpr125 |
| GPR126 | GPR126 | Gpr126 | Gpr126 |
| GPR128 | GPR128 | Gpr128 | Gpr128 |
| GPR133 | GPR133 | | Gpr133 |
| GPR143 | GPR143 | Gpr143 | Gpr143 |
| GPR144 | GPR144 | | Gpr144 |
| GPR157 | GPR157 | Gpr157 | Gpr157 |
| LPHN1 | LPHN1 | Lphn1 | Lphn1 |
| LPHN2 | LPHN2 | Lphn2 | Lphn2 |
| LPHN3 | LPHN3 | Lphn3 | Lphn3 |
| GPR156 | GPR156 | | |
| GPR158 | GPR158 | | |
| GPR179 | GPR179 | | |
| RAIG1 | GPRC5A | | |
| RAIG2 | GPRC5B | | |
| RAIG3 | GPRC5C | | |
| RAIG4 | GPRC5D | | |

REFERENCES

1. C G Tate, G F X Schertler (2009) *Curr Opin Struct Biol* 19, 386-395
2. Y Shibata, J F White, M J Serrano-Vega, F Magnani, A L Aloia, R Grisshammer, C G Tate (2009) *J Mol Biol* 390, 262-77
3. F Magnani, Y Shibata, M J Serrano-Vega, C G Tate (2008) *Proc Natl Acad Sci USA* 105, 10744-9
4. M J Serrano-Vega F Magnani, Y Shibata, C G Tate (2008) *Proc Natl Acad Sci USA* 105, 877-82.
5. A I Alexandrov, M Mileni, E Y Chien, M A Hanson, R C Stevens (2008) *Structure* 16, 351-9
6. P R Selvin (2000). *Nat Struct Biol* 7, 730-734
7. H Bazin, E Trinquet, G Mathis (2002) *J Biotechnol* 82, 233-250
8. A Keppler, H Pick, C Arrivoli, H Vogel, K Johnsson (2004) *Proc Natl Acad Sci USA* 101, 9955-9959
9. A Keppler, S Gendreizig, T Gronmeyer, H Pick, H Vogel, K Johnsson (2003) *Nat Biotechnol* 21, 86-89

The invention claimed is:

1. An assay for assessing the conformational stability of a membrane protein, comprising:
   (a) providing a sample comprising a first population and a second population of a membrane protein; wherein the membrane protein in the first population is labelled with a donor label and the membrane protein in the second population is labelled with an acceptor label, or the membrane protein in the first population is labelled with an acceptor label and the membrane protein in the second population is labelled with a donor label, and wherein the populations of membrane protein are provided in a solubilized form,
   (b) exposing the first and second populations of the membrane protein provided in the solubilized form to a denaturant or denaturing condition, and
   (c) assessing aggregation between membrane proteins of the first and second populations by activating the donor label to permit a distance-dependent interaction with the acceptor label, which interaction produces a detectable signal.

2. The assay of claim 1, wherein the first population and second population of the membrane protein are present in the sample in a 1:1 ratio.

3. The assay of claim 1, wherein the donor label is covalently attached to the membrane protein and the acceptor label is covalently attached to the membrane protein.

4. An assay for assessing the conformational stability of a membrane protein, comprising:
   (a) providing a sample comprising a membrane protein population, wherein the population of membrane protein is provided in a solubilized form,
   (b) exposing the membrane protein population to a denaturant or denaturing condition,
   (c) labelling one of the N-terminus or C-terminus of the membrane protein with a donor label and the other of the N-terminus or C-terminus of the membrane protein with an acceptor label, and
   (d) assessing aggregation of the membrane proteins in the population by activating the donor label to permit a distance-dependent interaction with the acceptor label, which interaction produces a detectable signal.

5. The assay of claim 1, wherein the interaction between the donor label and the acceptor label involves the transfer of energy from a donor fluorophore to an acceptor fluorophore.

6. The assay of claim 5, wherein the donor fluorophore is a lanthanide, optionally wherein the lanthanide is Terbium.

7. The assay of claim 5, wherein the acceptor fluorophore is EGFP or d2.

8. The assay of claim 1, wherein the interaction between the donor label and the acceptor label is a chemiluminescent reaction, optionally wherein the interaction between the donor label and the acceptor label involves the generation of singlet oxygen molecules that trigger a chemiluminescent reaction.

9. The assay of claim 1, wherein the donor label and/or acceptor label is directly attached or indirectly attached to the membrane protein.

10. The assay of claim 1, wherein the sample comprises one or more detergents selected from the group consisting of DDM, C11-maltoside, C10-maltoside, C9-maltoside, C8-maltoside, C11-glucoside, C10-glucoside, C9-glucoside, C8-glucoside, LDAO, and SDS.

11. The assay of claim 1, wherein the denaturant or denaturing condition is selected from one or more of heat, a detergent, a chaotropic agent or pH.

12. The assay of claim 1, wherein the membrane protein is a GPCR.

13. The assay of claim 12, wherein the sample provided in step (a) comprises a GPCR ligand, the ligand being one that binds to a GPCR when the GPCR is residing in a particular conformation.

14. The assay of claim 13, wherein the GPCR ligand is from the agonist class of ligands and the particular conformation is an agonist conformation, or the GPCR ligand is from the antagonist class of ligands and the particular conformation is an antagonist conformation.

15. A method for selecting a membrane protein with increased conformational stability, comprising:
(a) comparing the conformational stability of one or more mutants of a parent membrane proteins with the conformational stability of the parent membrane protein according to the assay of claim 1, and
(b) selecting one or more mutants that have increased conformational stability relative to the parent membrane protein.

16. The method of claim 15, comprising:
(a) providing one or more mutants of a parent membrane protein;
(b) assessing the conformational stability of the one or more mutants of the parent membrane protein;
(c) assessing the conformational stability of the parent membrane protein; and
(d) selecting one or more mutants of the parent membrane protein that have increased conformational stability compared to the conformational stability of the parent protein.

17. The method of claim 15, wherein the membrane protein has increased stability to any of heat, a detergent, a chaotropic agent or an extreme of pH.

18. A method for preparing a mutant GPCR, the method comprising:
(a) carrying out the method of claim 15,
(b) identifying the position or positions of the mutated amino acid residue or residues in the mutant membrane protein or membrane proteins which has been selected for increased stability, and
(c) synthesising a mutant membrane protein which contains a replacement amino acid at one or more of the positions identified.

19. The assay of claim 1, wherein the assay is used in drug screening.

20. The assay of claim 4, wherein the assay is used in drug screening.

* * * * *